United States Patent
Ábrahám et al.

(10) Patent No.: US 11,989,801 B2
(45) Date of Patent: May 21, 2024

(54) COMPUTER IMPLEMENTED COLOUR VISION TEST AND METHOD OF CALIBRATING THE COMPUTER IMPLEMENTED COLOUR VISION TEST

(71) Applicant: MEDICONTUR KFT., Zsámbék (HU)

(72) Inventors: György Ábrahám, Budapest (HU); Róbert Tamás Fekete, Budapest (HU); László Kontur, Budapest (HU); Péter Koncsár, Budapest (HU)

(73) Assignee: MEDICONTUR KFT., Zsámbék (HU)

( * ) Notice: Subject to any disclaimer, the term of this patent is extended or adjusted under 35 U.S.C. 154(b) by 57 days.

(21) Appl. No.: 17/786,732

(22) PCT Filed: Dec. 17, 2020

(86) PCT No.: PCT/HU2020/050061
§ 371 (c)(1),
(2) Date: Jun. 17, 2022

(87) PCT Pub. No.: WO2021/123850
PCT Pub. Date: Jun. 24, 2021

(65) Prior Publication Data
US 2023/0032436 A1    Feb. 2, 2023

(30) Foreign Application Priority Data

Dec. 18, 2019  (HU) .................................... P1900433
Dec. 19, 2019  (EP) .................................... 19217946
Jul. 27, 2020  (HU) .................................... P2000245

(51) Int. Cl.
*G06T 11/00* (2006.01)
*A61B 3/00* (2006.01)
(Continued)

(52) U.S. Cl.
CPC .......... *G06T 11/001* (2013.01); *A61B 3/0041* (2013.01); *A61B 3/022* (2013.01); *A61B 3/06* (2013.01)

(58) Field of Classification Search
CPC ......... A61B 3/0041; A61B 3/06; A61B 3/066; G06T 11/001
See application file for complete search history.

(56) References Cited

U.S. PATENT DOCUMENTS 5,946,075 A * 8/1999 Horn ....................... A61B 3/066
                                                    351/237
6,210,006 B1 * 4/2001 Menozzi ................ A61B 3/032
                                                    351/242
(Continued)

FOREIGN PATENT DOCUMENTS

JP           2014220744 A  * 11/2014
WO    WO-2005013806 A2 *   2/2005  ............. A61B 3/032

*Primary Examiner* — Charles Tseng
(74) *Attorney, Agent, or Firm* — Olson & Cepuritis, Ltd.

(57) ABSTRACT

Method of calibrating a computerised colour vision test and method of testing colour vision on a computer The invention relates to a method of calibrating a colour vision test for testing colour vision under given ambient lighting conditions, which colour vision test is to be displayed on a colour display (12) of a computer (10) having at least one input interface (14), characterised by displaying a calibration test on the display (12) under given ambient lighting conditions to a person with normal colour vision before starting the colour vision test, displaying within at least one measuring region (31) of the display (12) a colour determination task requiring user input as a part of the calibration test, reading the user input through at least one input interface (14) of the computer (10), evaluating the read user input and determining as a result of the evaluation a display error resulting from a combination of a colour reproduction capability of the display (12) and an effect of the ambient lighting conditions (Continued)

Figure 1:
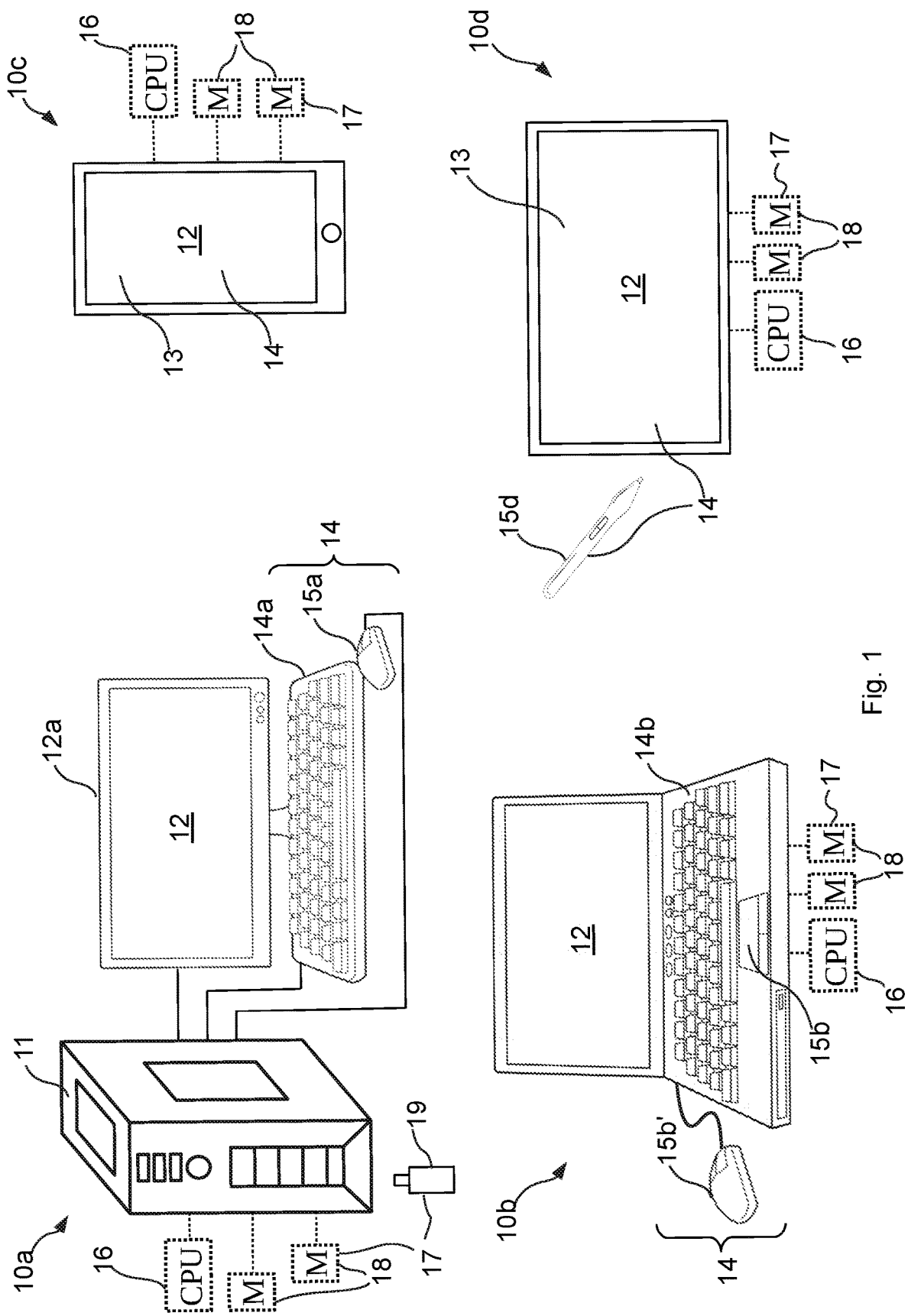

on colour vision, and determining a modification to the colour vision test from the display error that corrects the colour vision test with respect to the display error. The invention further relates to a method of testing colour vision using the calibration method, as well as to a computer and computer program configured for performing such methods. The invention further relates to a colour discrimination test, to a colour identification test and to a combination of the two tests.

20 Claims, 15 Drawing Sheets

(51) Int. Cl.
*A61B 3/02* (2006.01)
*A61B 3/06* (2006.01)

(56) References Cited

U.S. PATENT DOCUMENTS

| | | | |
|---|---|---|---|
| 2010/0188639 A1* | 7/2010 | Carda | A61B 3/066 |
| | | | 351/242 |
| 2014/0340644 A1* | 11/2014 | Haine | A61B 3/066 |
| | | | 351/239 |

* cited by examiner slider:

r:   205              255         255              255
g:   255              255         255-y            205
    |-----------------|-----------|----------------|
y:  -50               0           y                +50 display:
                                  +Δ
                                  → r:   205              255         255              255
g:   255              255         255-(y+Δ)        205
    |-----------------|-----------|----------------|
r-g: -50              0           y→(y')=y+Δ       +50
                                       ↓

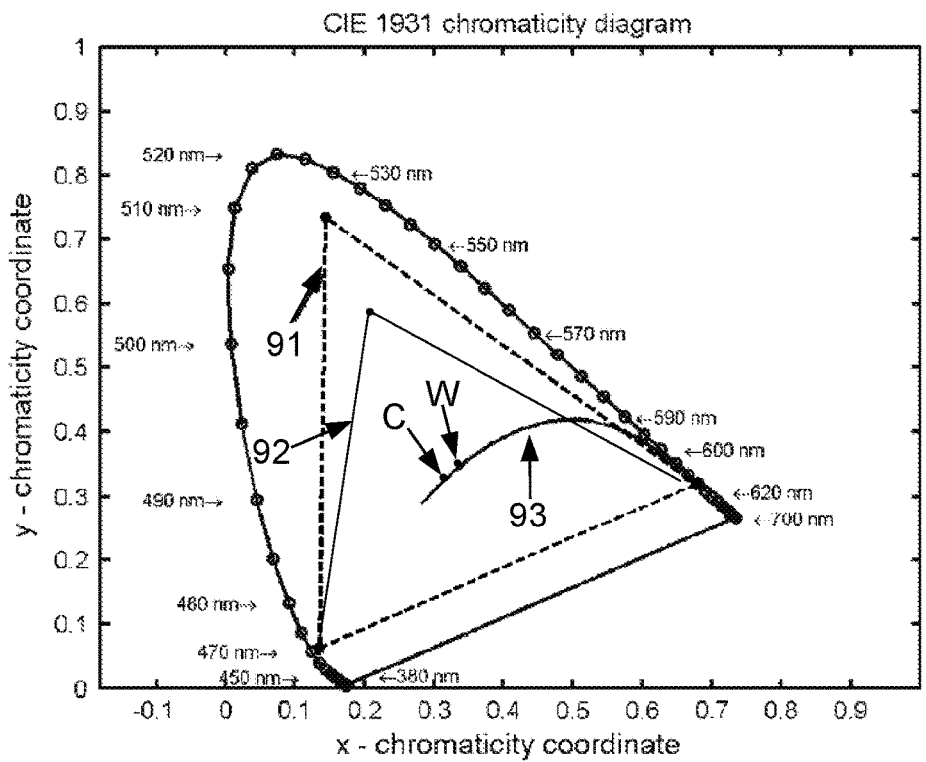
Fig. 9
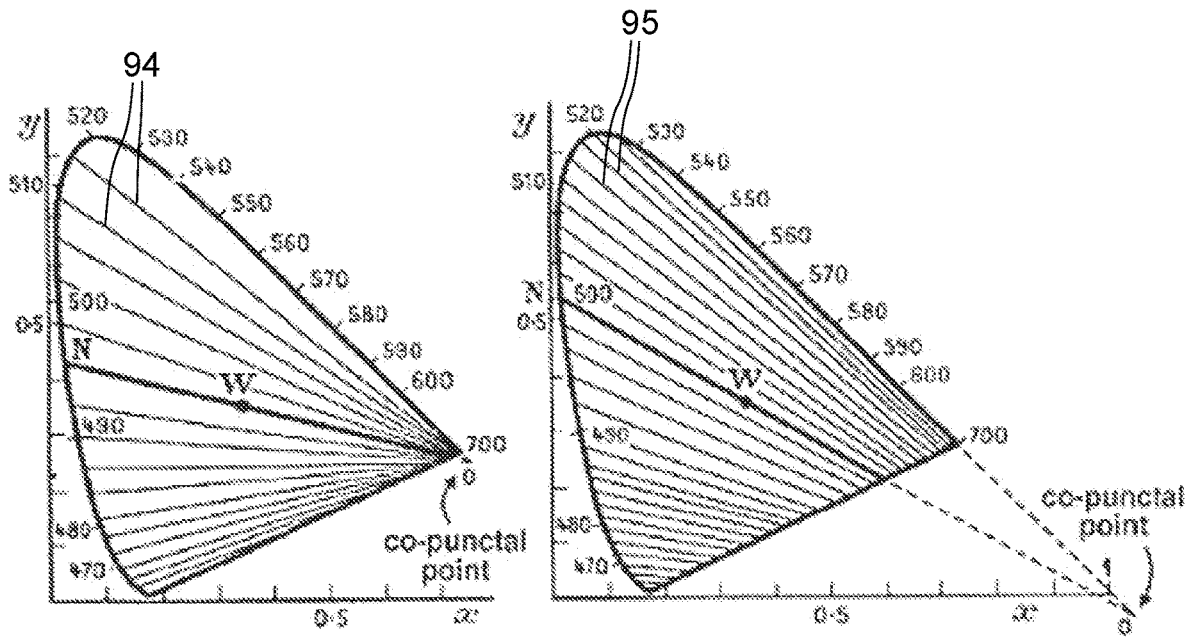
Fig. 10a                      Fig. 10b

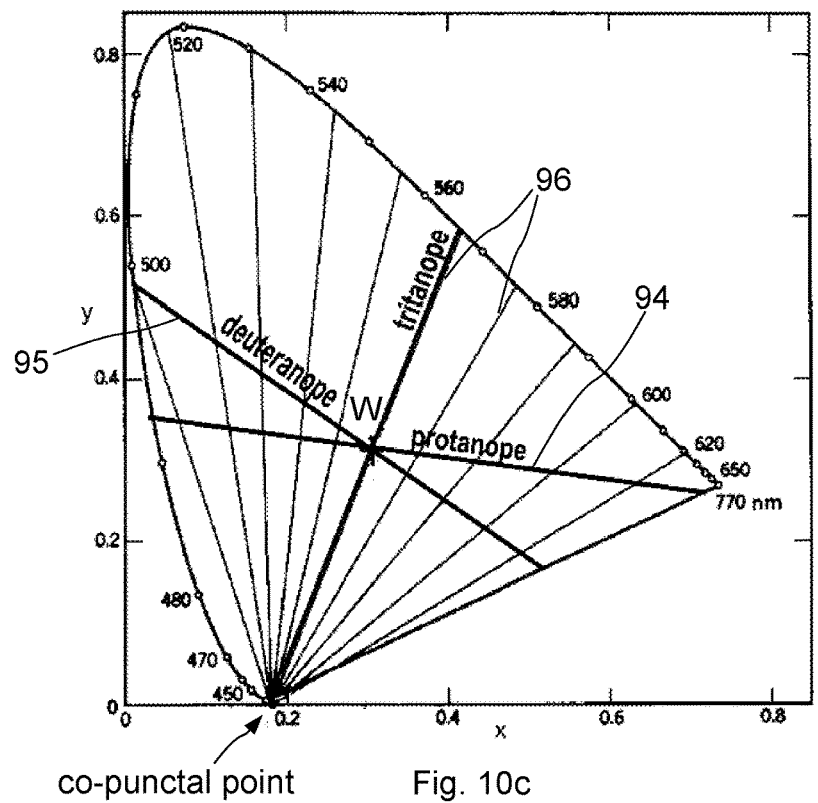
co-punctal point     Fig. 10c
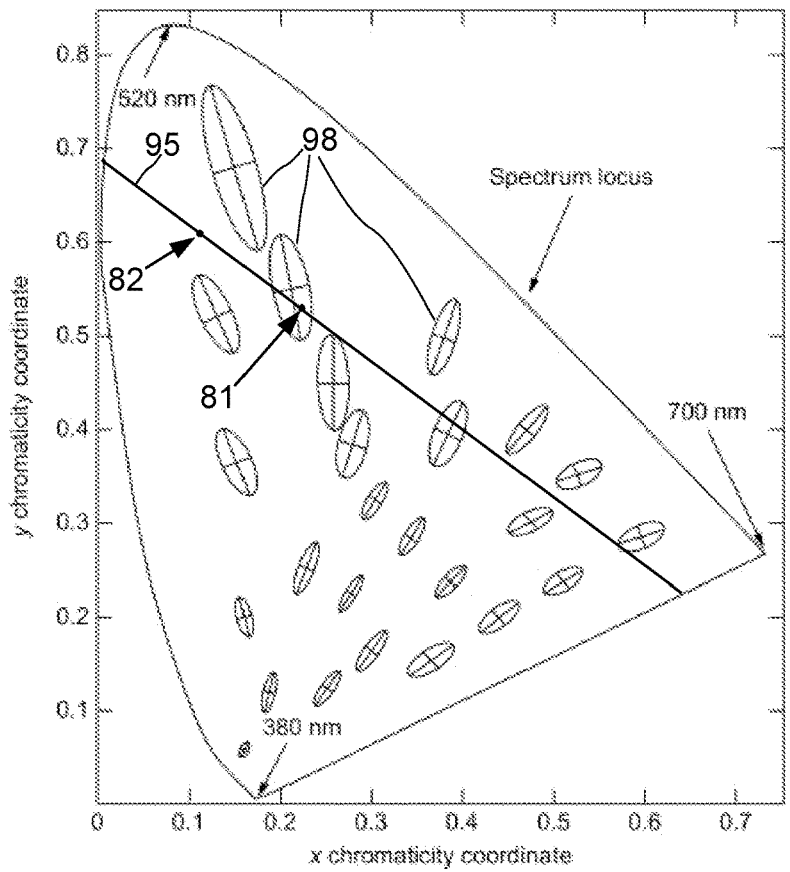
Fig. 11

COMPUTER IMPLEMENTED COLOUR VISION TEST AND METHOD OF CALIBRATING THE COMPUTER IMPLEMENTED COLOUR VISION TEST

CROSS-REFERENCE TO RELATED APPLICATION

This application is a U.S. National Stage of PCT/HU2020/050061, filed Dec. 17, 2020, which claims priority to Hungarian Application No. P2000245, filed Jul. 27, 2020, European Application No. 19217946.3 filed Dec. 19, 2019 and Hungarian Application No. P1900433, filed Dec. 18, 2019, each of which is incorporated herein by reference.

The invention relates to a method of testing colour vision of a person with colour vision deficiency, which colour vision test is intended to be displayed on a colour display of a computer having at least one input interface.

The invention further relates to a method of calibrating such a colour vision test for testing the colour vision of a person with colour vision deficiency.

The invention also relates to a computer program configured for performing such methods and devices storing this program.

In the context of the present invention computer is understood to mean an electronic device comprising hardware and software components that is for receiving, storing, processing and transmitting data, and program code containing appropriate computer commands for performing these tasks. The computer typically has at least one processor, memory, and peripherals, i.e. input and output interfaces, the latter of which may be provided in an integrated way, such as in the form of a touchscreen. In the context of the present invention a computer is particularly a desktop PC (Personal Computer), laptop, tablet, smartphone, etc.

Colour vision is ensured by certain receptors located on the retina, namely the cones providing daylight vision. There are three types of such receptors based on their spectral sensitivity. L-cones are sensitive mainly to the long wave (red) range of the spectrum. M-cones are sensitive to light in the medium wavelength range (green), while S-cones are sensitive to light in the shortwave range (blue). The sense of colour is created on the basis of the relative values of the stimuli transmitted by the colour-sensing L, M and S-cone receptors.

The two most important characteristics of colour vision are:

the ability to discriminate colour hue or tone (colour discrimination), which is the ability to differentiate between two different colours; and the colour identification ability (colour identification), which is the ability with which a person is able to correctly name certain colours or hues.

Colour vision deficiency (also called colour blindness) is caused by the spectral sensitivity curves of colour blind persons deviating to smaller and greater extents from those of normal (healthy) people, accordingly the most frequent forms of colour vision deficiency are protanomaly, protanopia, deuteranomaly and deuteranopia. The colour-sensing problem protanomaly is caused by the spectral sensitivity of the L-cones being closer to the spectral sensitivity of the M-cones than in the case of those with normal colour vision. As a consequence, the difference between the stimuli of the L and M-cones is reduced, and this results in a deterioration of the ability to differentiate between colours. In extreme cases the spectral sensitivity of the L-cones is shifted to such an extent that it coincides with the spectral sensitivity curve of the M-cones, which is referred to as protanopia.

In the case of deuteranomaly the spectral sensitivity of the M-cones lies closer to the spectral sensitivity of the L-cones, than in the case of those with normal colour vision. The result is similar to the previous case: the difference between the stimuli of the L-cones and M-cones drops, i.e. the ability to differentiate between colours deteriorates in this case too. Deuteranopia is the condition when the spectral sensitivity curve of the M-cones is shifted to such an extent that it coincides with the spectral sensitivity curve of the L-cones.

Approximately 23% of people suffering from colour vision deficiency have protanomaly, 73% have deuteranomaly, and about 4% have severe colour blindness (protanopes and deuteranopes). The most severe form of colour vision deficiency monochromasia, total colour blindness is extremely rare. The blue sensitive receptor, the S-cone is very rarely defective. Damage to this receptor is usually caused by illness or intoxication, and when the cause is eliminated colour vision becomes normal once again. Due to this almost 100% of people with defective colour vision have protanomaly, deuteranomoly, protanopia or deuteranopia.

Computers are being used increasingly to test colour vision. Patients are asked to perform various colour tests on these computers to determine if they have any colour vision deficiency and, if so, its type and severity. Such tests include the screen versions of the well-known pseudochromatic test books (e.g. Ishihara, Rabkin, Dvorin, Velhagen, Hardy, HRR) and of various other colour discrimination tests. Even though electronic screens display colours that differ from screen type to screen type and which are different to those in printed or painted tests, their use is still spreading, partly because of their increasingly better colour reproduction abilities and partly because of their easy access. A further advantage is that electronic display devices make it possible for persons located at remote places around the world and potentially having impaired colour vision, to be able to diagnose themselves (or have telediagnosis performed), on the basis of which a diagnosis may be determined and suitable correction device (colour filter glasses) may be ordered on the internet.

However, the different colour reproduction capabilities of electronic displays represent a great problem, as they have different primary colours depending on the manufacturer, both with respect to the characteristic wavelength and the spectra of the primary colours.

Another problem is the degree of adaptation of the tested person's eye to the ambient light. It is not indifferent whether the sensitivity of each of the three receptors (red, green, blue) of a human eye is the same, or significantly different from each other as a result of different ambient lighting conditions.

The same eye sees colours in different ways in different states of adaptation. For example, the human eye sees different colour shades in incandescent light, sunlight, fluorescent light, and in light emitted by LEDs. Due to this if a colour vision test program is displayed on a computer monitor, laptop, tablet or smartphone, then depending on the device's colour reproduction capability and the degree of adaptation of the tested person's eye to the ambient lighting conditions the test may produce incorrect results and therefore an incorrect diagnosis.

There are further problems associated with the current computerized (and non-computerized) colour vision tests.

The most well-known colour vision test is the Ishihara test named after Dr Shinobu Ishihara. The test consists of a number of coloured plates, called Ishihara plates, each of which contains a circle of dots appearing randomized in colour and size. Within the pattern are dots which form a number or shape clearly visible to those with normal colour vision, and invisible, or difficult to see, to those with a red-green colour vision defect. Other plates are intentionally designed to reveal numbers only to those with a red-green colour vision deficiency, and be invisible to those with normal red-green colour vision. The full test consists of 38 plates, but the existence of a severe deficiency is usually apparent after only a few plates.

The Ishihara test makes use of the fact that people with red-green colour vision deficiency tend to differentiate between these colours based on brightness. The human eye has a lower light sensitivity in the range of lower frequencies, whereby red colour (lower frequency) appears darker than green (higher frequency) in the same lighting conditions. People with red-green colour vision deficiency have difficulty in differentiating between red and green colours, hence their brain learns to differentiate based on brightness instead of hue. The Ishihara test varies the brightness and the colours of the random dots within each plate. The applied colours are pseudo-isochromatic, which means that these colours appear isochromatic (as having the same hue) to subjects with colour-vision abnormality, however, people with normal colour vision can differentiate between at least two different hues. In the case of the Ishihara test confusion of red and green colours are detected which indicate deutan (deuteranomaly and deuteranopy) and protan (protanomaly and protanope) colour deficiency. The colours used within each plate are mixed colours which may also contain blue as a component, however the information (number or sign) is either hidden based on the red and green colour component or based on the brightness of the dots. People with normal colour vision see the different hues of the applied red and green colour components and their brain will detect numbers and signs by automatically connecting the different hues of red and separately connecting the different hues of green, thus they will detect the information that is coded by colour. In contradistinction, people with red-green colour deficiency are unable (or only limitedly able) to use this information, instead the brain of these people will connect the dots appearing in the same or similar brightness, whereby red-green colour blind people will detect information that is coded by brightness.

Attempts have been made to implement the Ishihara test on a computer display, however, the special colour and brightness of each individual dot cannot be reproduced on a computer display, even if it is well calibrated, which can lead to a poor diagnosis.

The inventors have realised further problems with the Ishihara test and its computer implementation. The inventors have realised that the Ishihara test relies on image recognition which is a learned process performed by the brain. As a result the Ishihara test does not only measure the brain's ability to discriminate between the colours red and green, it automatically measures the brain's ability to connect similar dots and to interpret it as an image (number or sign). The effect of the latter cannot be removed from the measurement result, meaning that somebody with impaired image recognition, or a child who has not yet developed these skills will score poorly on these tests regardless of their colour vision.

The inventors have realised that a further problem with the Ishihara test is that dots containing different hues of red and green colour and also having significantly different brightness from each other are closely packed on each plate, whereby when a person tries to detect a number or signed hidden within the plurality of these dots his or her gaze will wander within the dotted plate. As the person's gaze traverses the quasi random dots too rapid changes in the sensed colour and brightness can have a negative effect on the neural system and may cause epilepsy in people who are prone to this. The inventors have found that this problem is aggravated when the Ishihara test (or any other similar test) is displayed on a computer display, especially if the brightness of the screen is set to a high level.

The inventors have further realized that due to the limited colour displaying ability of computer displays when the Ishihara test is implemented on a computer the severity of colour vision deficiency cannot be reliably diagnosed. In particular, severely deuteranomale, close to deuteranope, and deuteranope people cannot be distinguished from people with a medium (moderately severe) deuteranomaly. Similarly, severely protanomale, close to protanope, and protanope people cannot be distinguished from people with a medium (moderately severe) protanomaly.

The inventors have further realised that the Ishihara-type tests can only measure a person's ability to discriminate between colours, however the colour identification ability of a person maybe impaired separately from his or her colour discrimination ability. This is particularly the case for people with colour vision deficiency who have received corrective lenses (comprising colour filters) for restoring normal colour vision, whereby these people may score well on colour discrimination tests, however most of the commercially available corrective lenses do not improve colour identification only colour discrimination, which means that the person wearing the corrective lenses will see red and green colour differently from each other, but will still not see these colours as red and green (i.e. the colours that a person with normal colour vision would perceive). There is thus a need to measure a person's ability to identify colours as well.

It is an objective of the present invention to provide a method and computer program to overcome the problems associated with the prior art, in particular, the problems described above.

A first aspect of the invention is based on the recognition that a person with normal colour vision can contribute to making a correct diagnosis of a person with colour deficiency who is present at the same location as the colour blind person being tested and who uses the same device under the same ambient lighting conditions, whereby the measured results provide information both about the device and about the ambient lighting conditions. The same test may be performed on the reference person with normal colour vision as is then performed on the patient to be measured, or a different test may be separately performed for the purpose of calibration.

The colour vision test may be modified in view of the calibration measurement results of the person with normal colour vision in order to take into consideration the display's colour reproduction capability and the effect of the ambient lighting on colour vision. Two things may be done with the measurement results of the person with normal colour vision: the results, such as the monitor's R/G/B settings, may be used when performing a given task for the ad hoc modification and tuning of the parameters of the software colour vision test performed on the patient, in this way the test for examining colour vision is now displayed to the patient with modified parameters. The other possibility is that the displaying of the colour vision test is not modified, however a different diagnosis is made from its results after performing the necessary correction.

The above objectives are achieved in accordance with the invention by the calibration method according to claim 36.

The invention further relates to a colour vision testing method according to claim 44 which uses the calibration method according to the invention.

The invention further relates to a computer according to claim 47 configured to perform the measuring method, and a computer program according to claim 48.

A second aspect of the invention is based on the recognition that a colour discrimination test can be provided which does not rely on image recognition ability of a tested person and wherein a plurality of pseudo-isochromatic dots are presented in distinct regions of the display screen, such that the changes in hue and brightness within a single region is within an acceptable range so as not to provoke epileptic seizures. Accordingly, the invention further relates to a colour vision test according to claim 1.

A third aspect of the invention is based on the recognition that a colour identification test can be provided which detects severe deuteranomaly and severe protanomaly in a very reliable way, whereby this test is suitable for supplementing a colour discrimination test in order to better differentiate between moderately sever and severe cases of deuteranomaly/protanomaly. Accordingly, the invention further relates to a colour vision test according to claim 13.

A fourth aspect of the invention is based on the recognition that a colour identification test can be provided to supplement a colour discrimination test in order to distinguish severe cases colour vision deficiency from mild and moderate cases. Accordingly, the invention further relates to a colour vision test according to claim 32.

Advantageous embodiments of the invention are defined in the attached dependent claims.

Figure 2A:
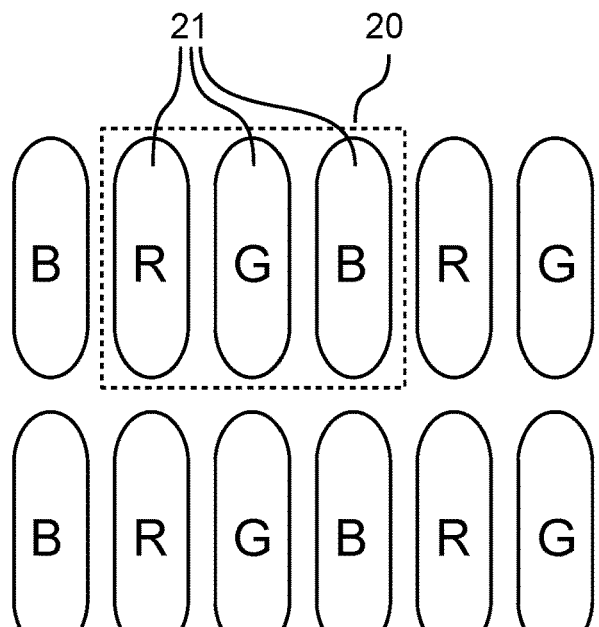
Figure 2B:
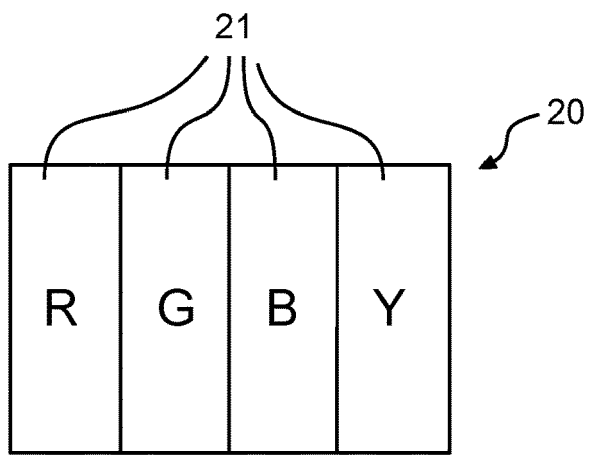
Figure 2C:
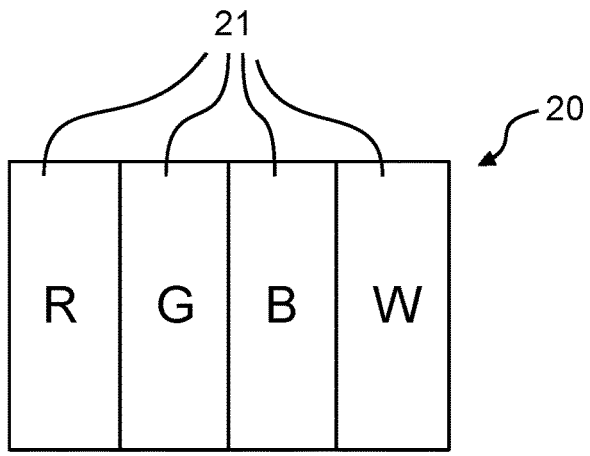
Figure 3:
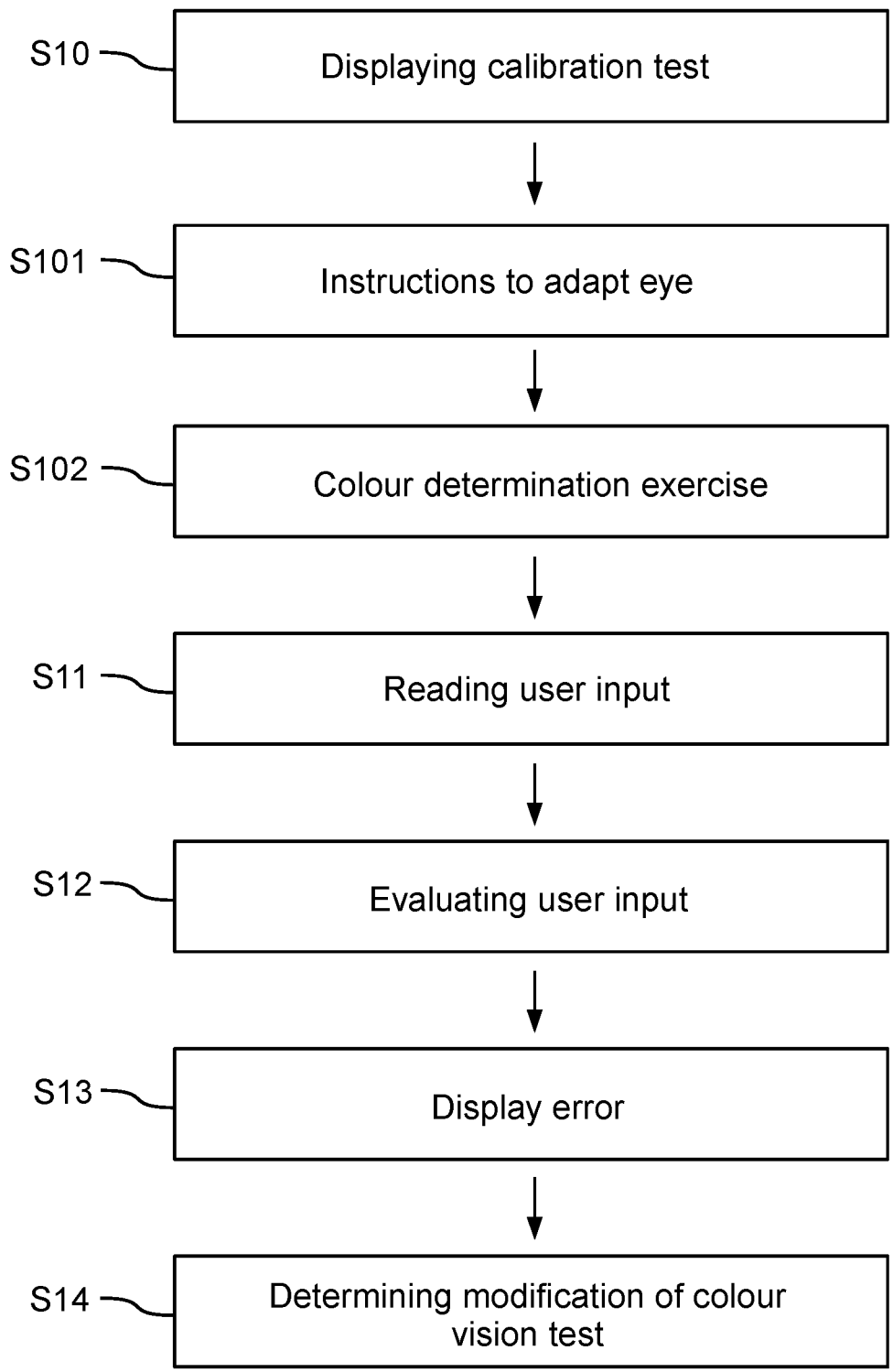
Figure 3A:
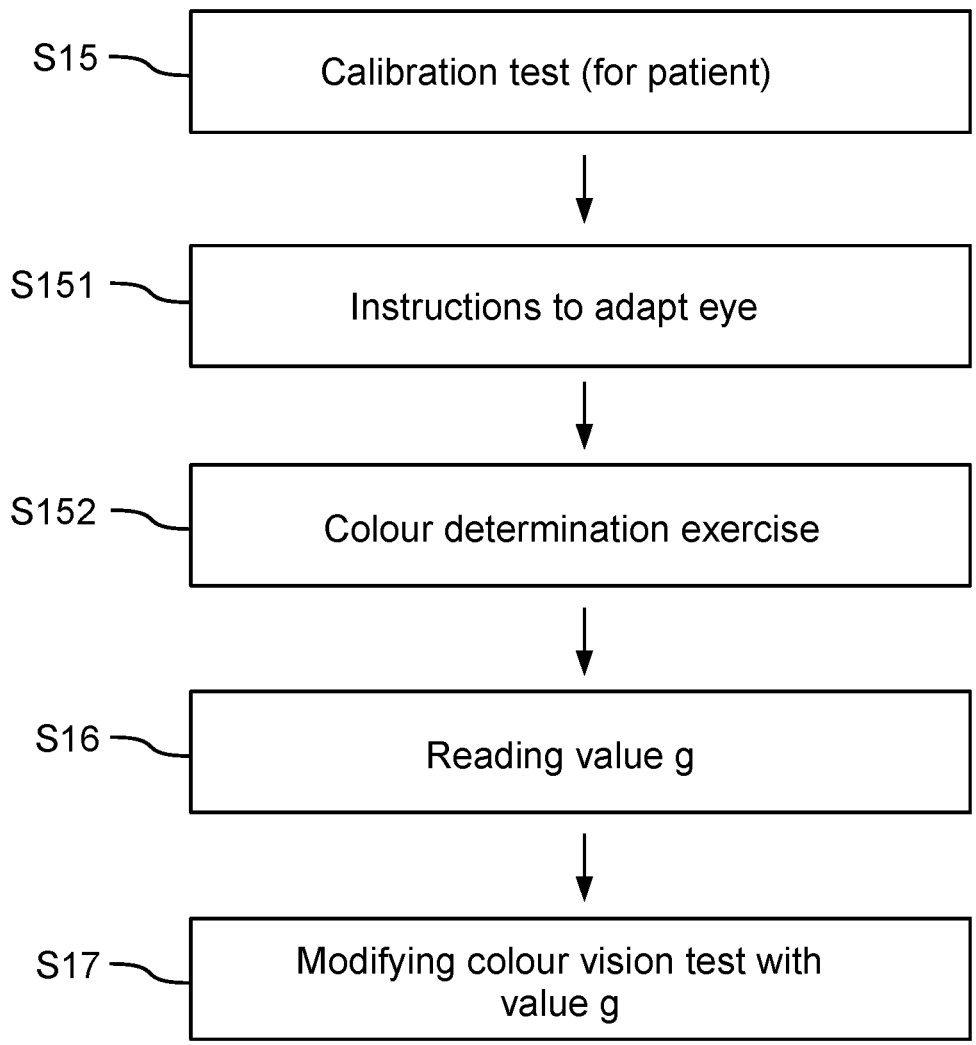
Figure 4:
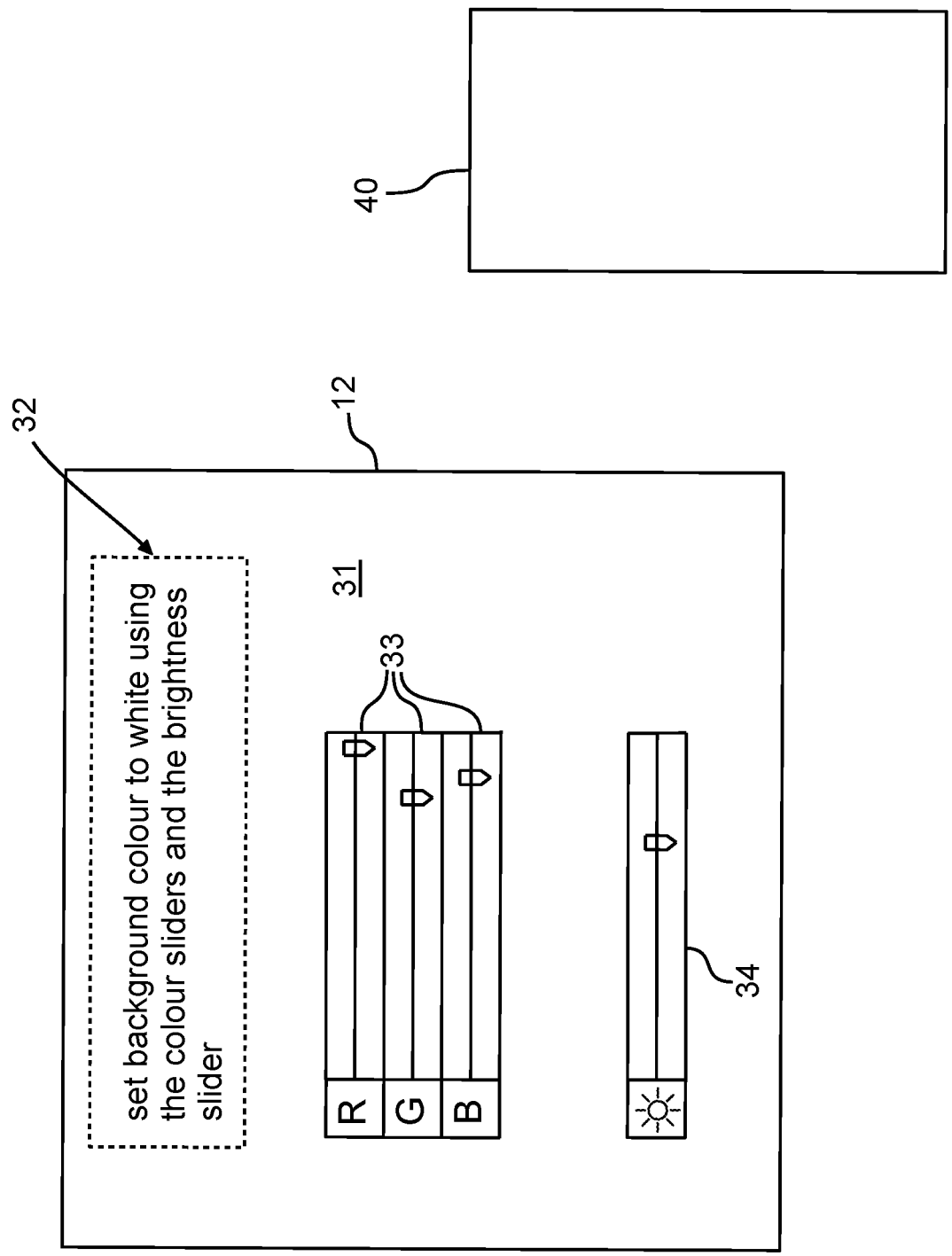
Figure 5:
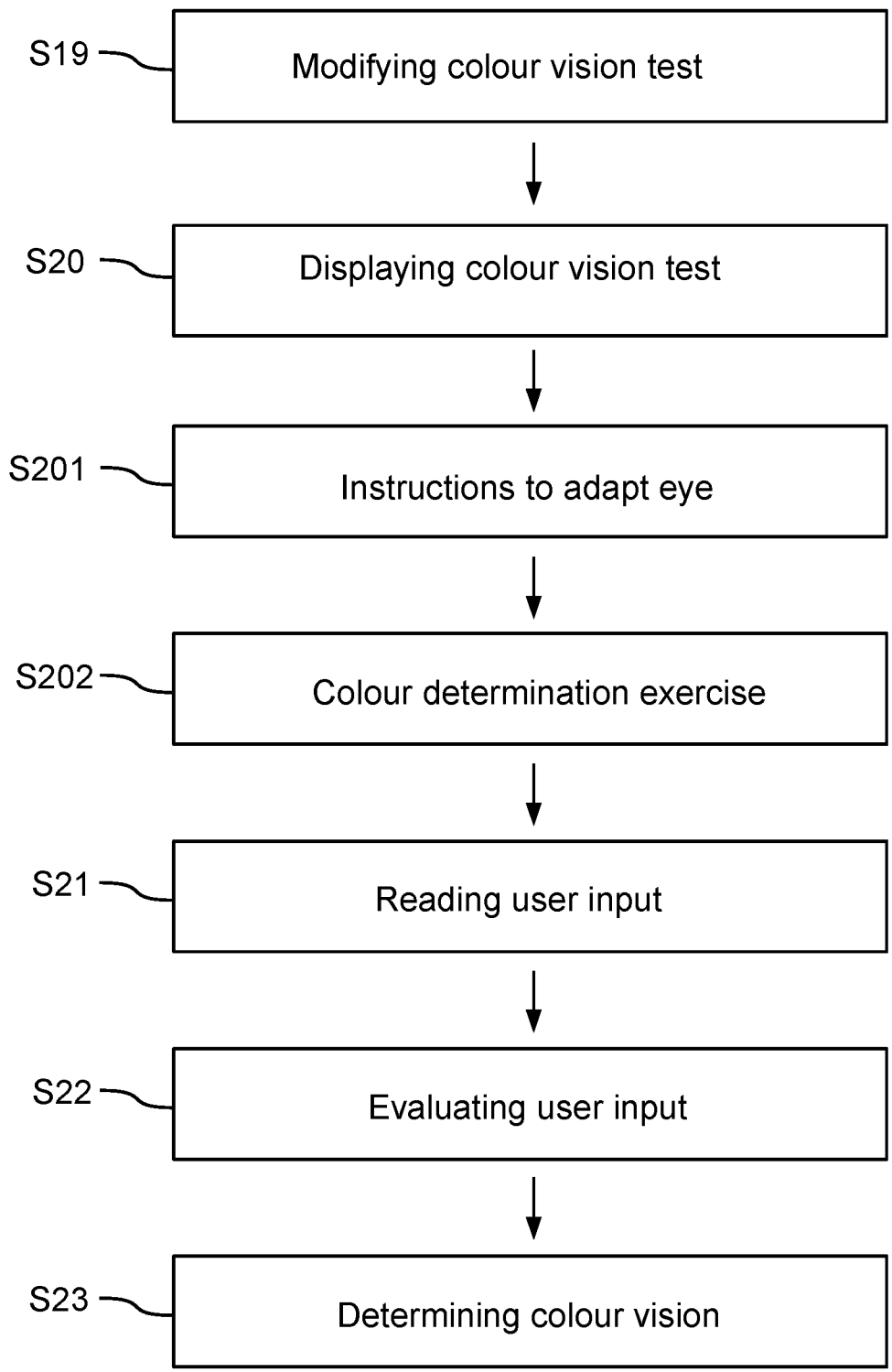
Figure 6:
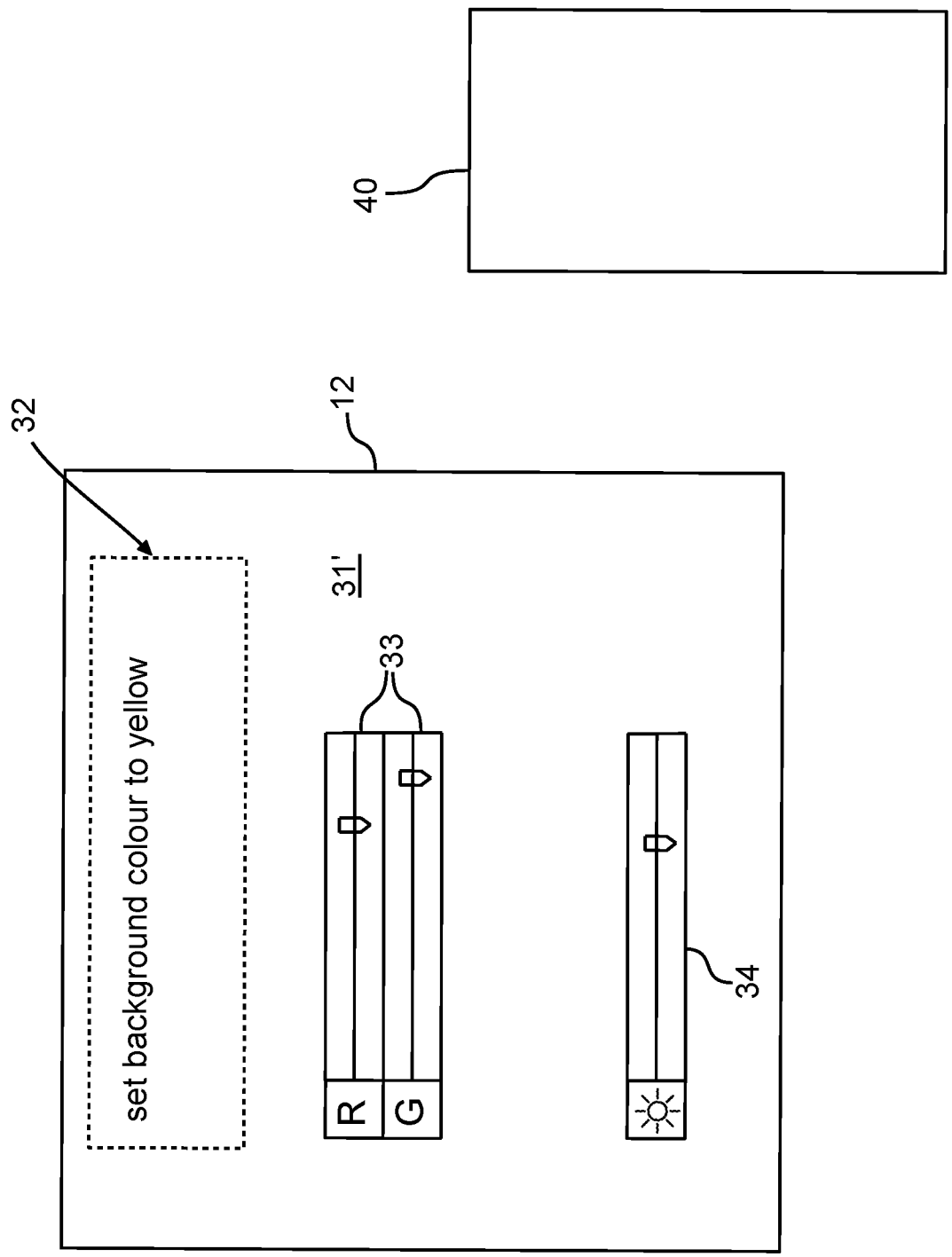
Figure 7:
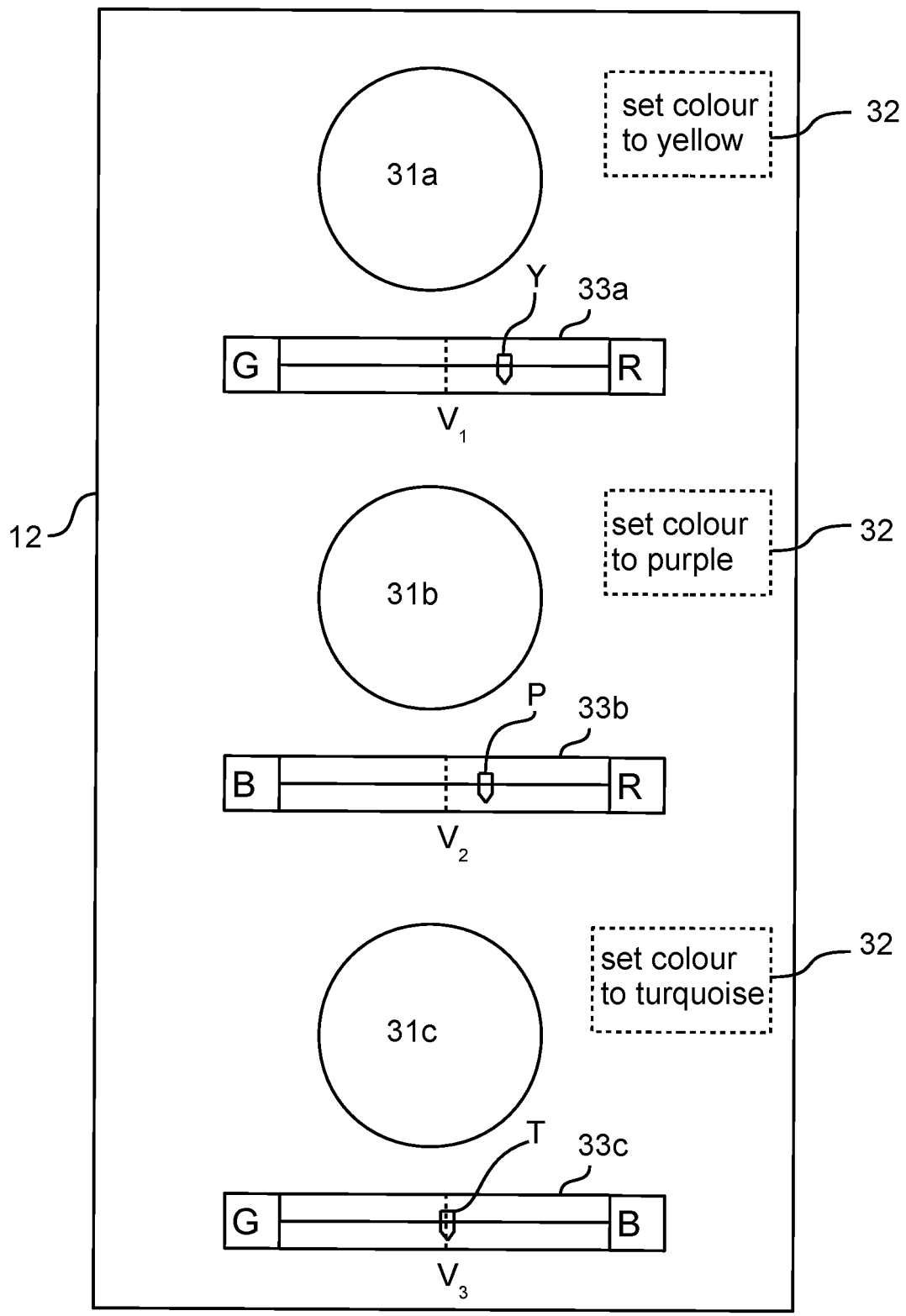
Figure 7A:
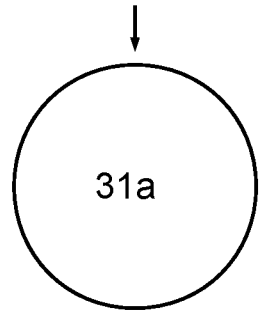
Figure 8:
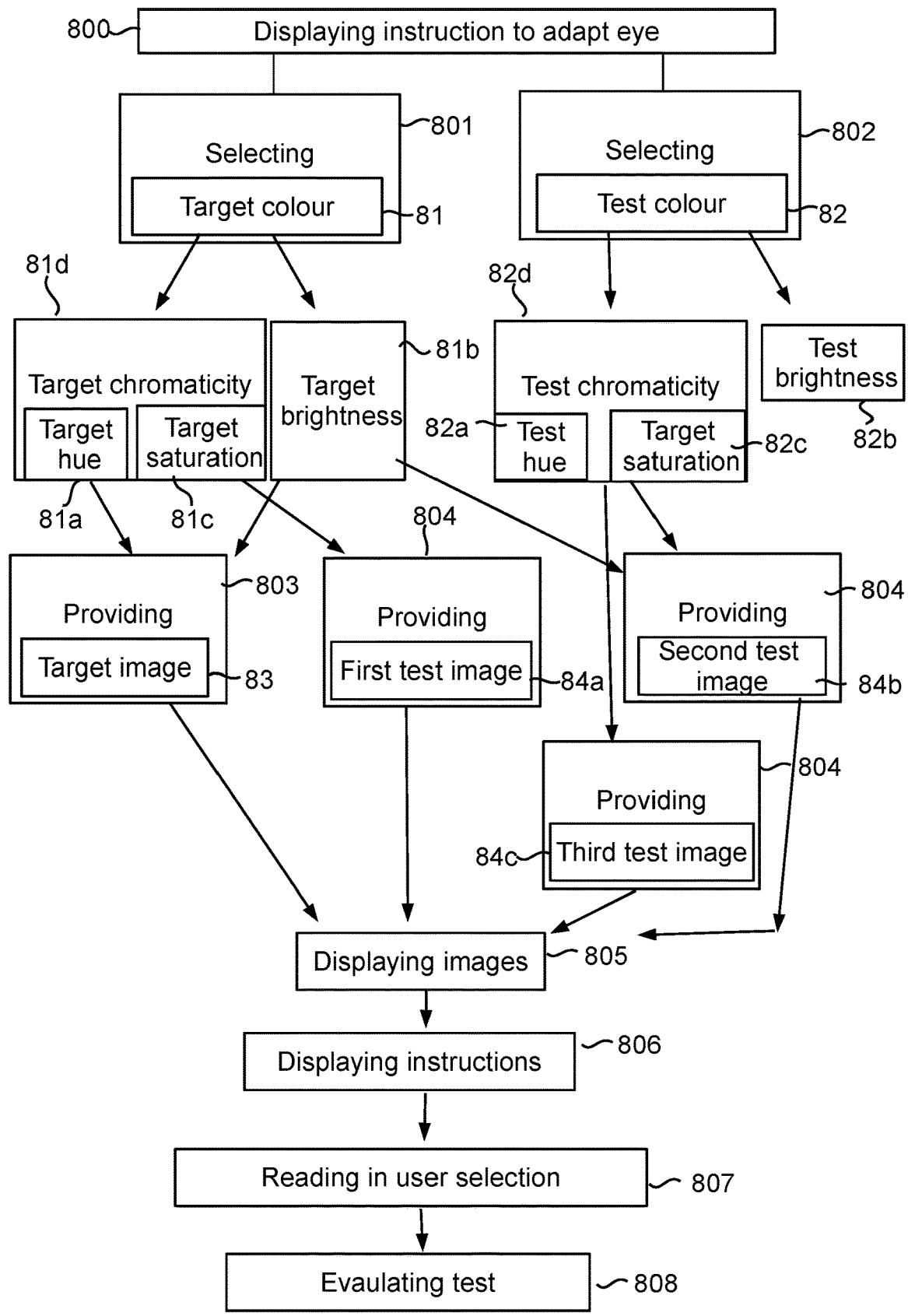
Figure 12:
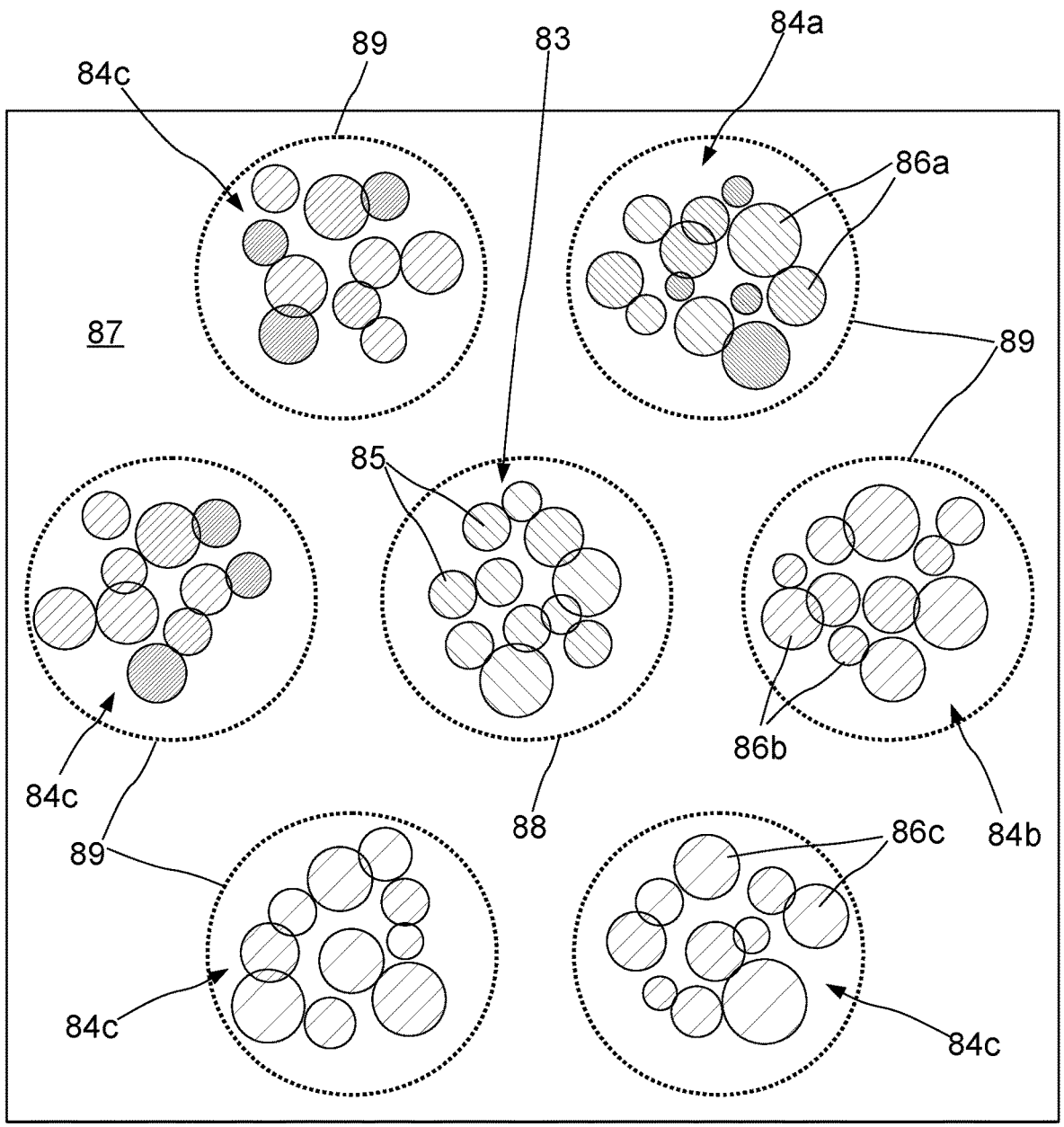
Figure 13:
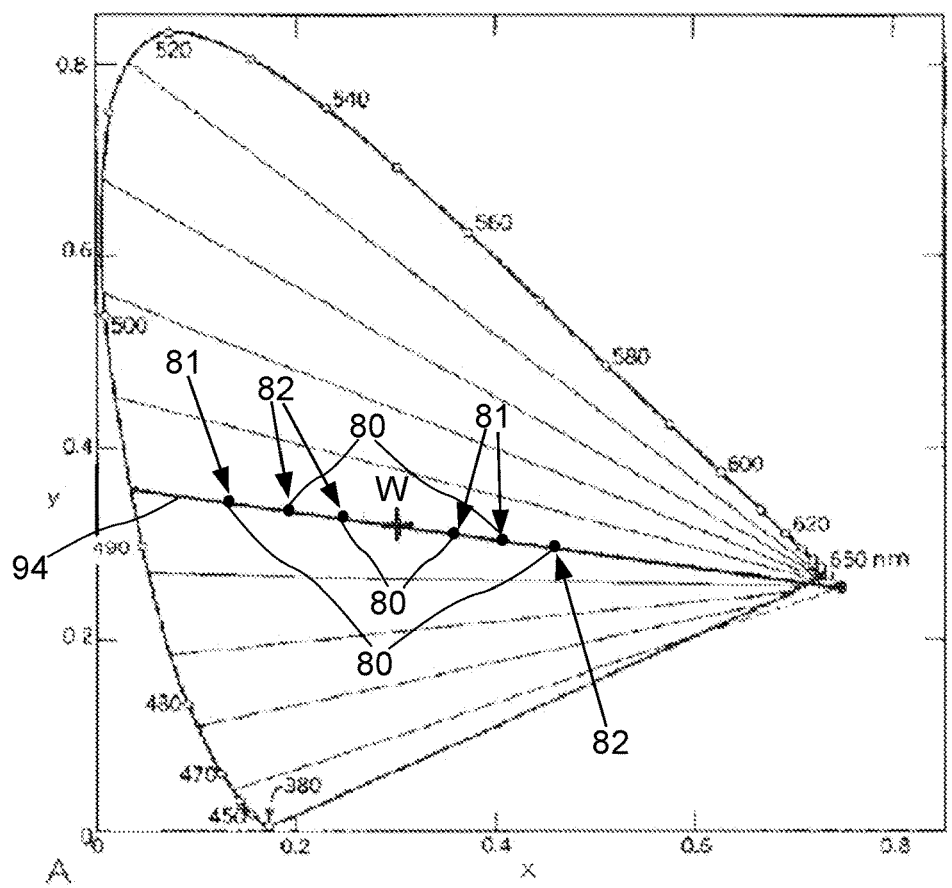
Figure 14:
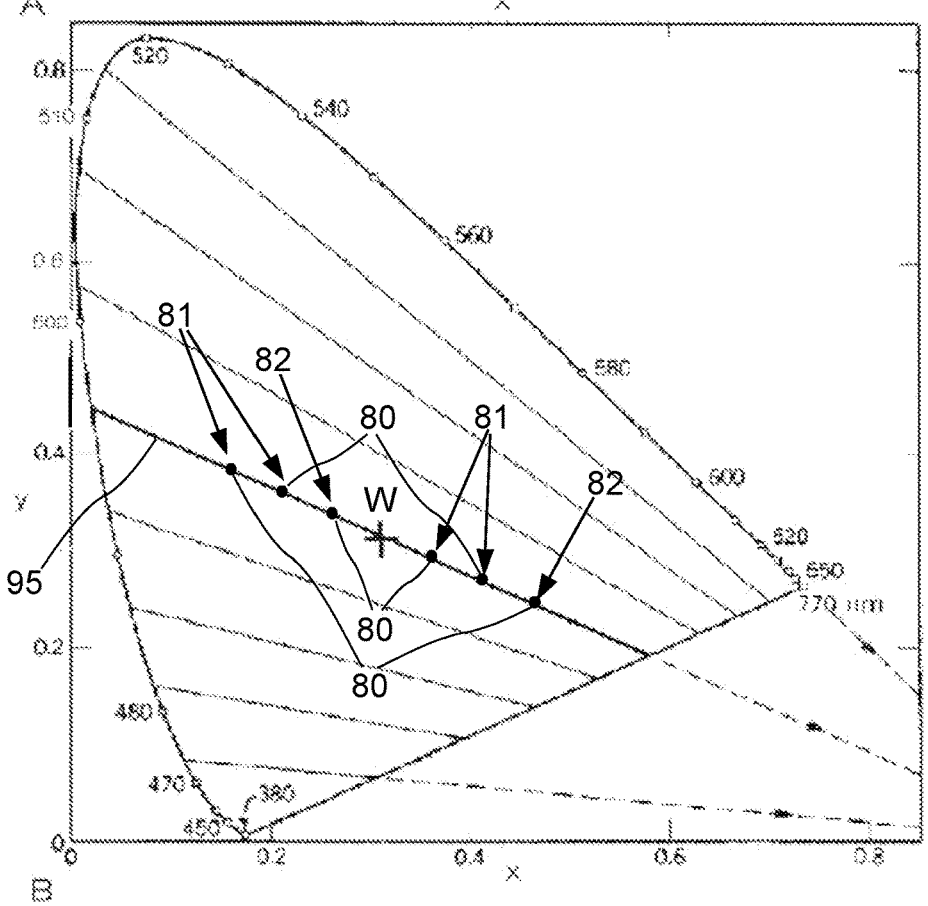
Figure 15:
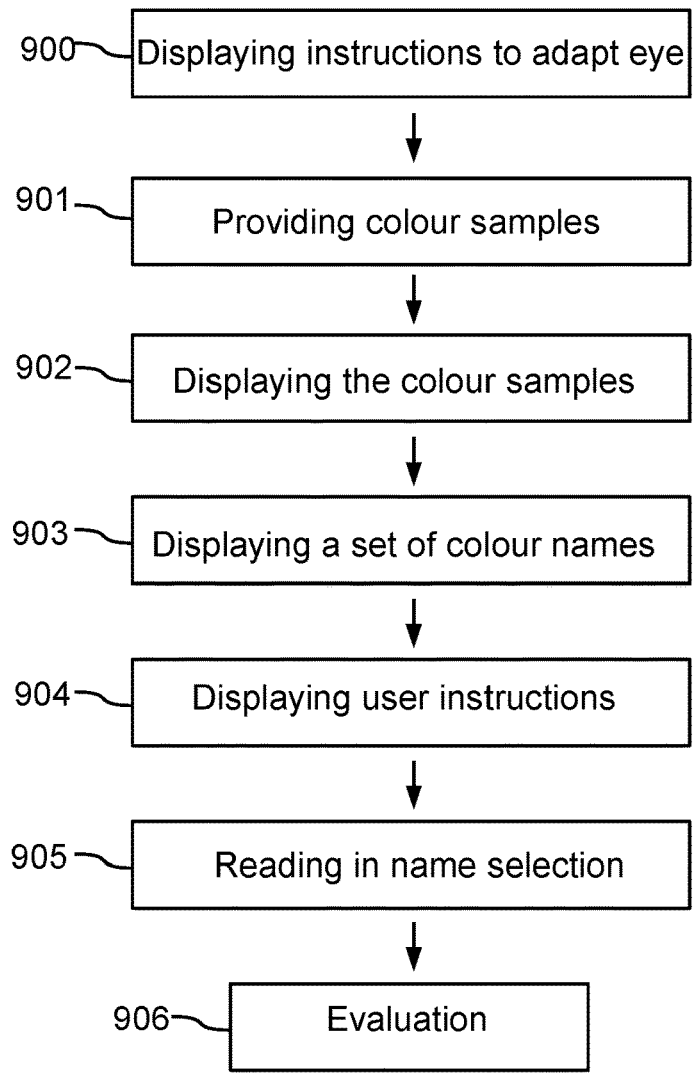
Figure 16:
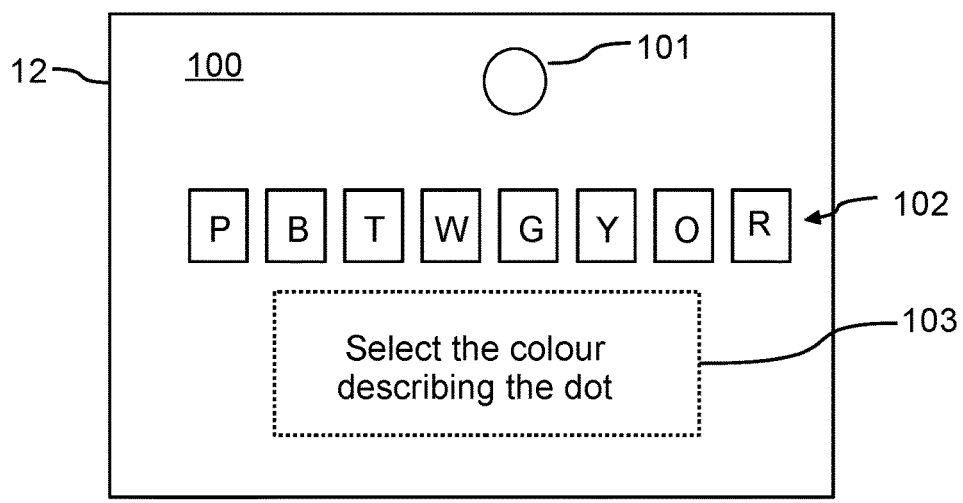

Further details of the invention will be explained by way of exemplary embodiments with reference to the Figures, wherein:

FIG. 1 depicts a schematic view of exemplary computers for implementing the method according to the invention, FIG. 2*a* depicts a schematic view of the subpixels of an exemplary display, FIG. 2*b* depicts a schematic view of the subpixels of a different exemplary display, FIG. 2*c* depicts a schematic view of the subpixels of a third exemplary display, FIG. 3 depicts a flow diagram of an embodiment of the calibration method according to the invention, FIG. 3*a* depicts a flow diagram presenting the supplementary steps of an exemplary embodiment of the calibration method according to the invention, FIG. 4 depicts a schematic screen image of an exemplary embodiment of a calibration test according to the invention, FIG. 5 depicts the flow diagram of an exemplary embodiment of a colour vision test according to the invention, FIG. 6 depicts a schematic screen image of an exemplary embodiment of a colour vision test according to the invention, FIG. 7 depicts a schematic screen image of a different exemplary embodiment of a colour vision test according to the invention, FIG. 7*a* depicts an illustrative guide for correcting the displaying of the colour vision test according to FIG. 7, FIG. 8 is a flow diagram of a preferred embodiment of a colour vision test, FIG. 9 is a CIE chromaticity diagram showing the colour gamuts of various displays, FIG. 10*a* is a CIE chromaticity diagram showing protanope confusion lines, FIG. 10*b* is a CIE chromaticity diagram showing deuteranope confusion lines, FIG. 10*c* is a CIE chromaticity diagram showing tritanope confusion lines, FIG. 11 is a CIE chromaticity diagram showing MacAdam ellipses, FIG. 12 is an illustration of a screen image of an exemplary colour discrimination test displayed on a display of a computer, FIG. 13. is a CIE chromaticity diagram showing target colour and test colour pairs selected from a protanope confusion line, FIG. 14. is a CIE chromaticity diagram showing target colour and test colour pairs selected from a deuteranope confusion line, FIG. 15 is a flow diagram of another preferred embodiment of a colour vision test, and FIG. 16 is an illustration of a screen image of an exemplary colour identification test displayed on a display of a computer.

FIG. 1 shows a schematic view of exemplary computers 10 for implementing the methods according to the invention. Reference sign 10*a* designates a desktop PC, which is provided with peripherals in the conventional way, such as a monitor 12*a* with a display 12 and input interfaces 14, in the present case keyboard 14*a* and mouse 15*a*. Naturally the PC 10*a* may also have other input interfaces 14 and peripherals.

Reference sign 10*b* designates a laptop, which has a built in display 12, built in keyboard 14*b* and built in mouse 15*b*, as input interfaces 14, in addition the exemplary laptop 10*b* shown in FIG. 1 also has an external mouse 15*b*'. Naturally, the laptop 10*b* may also have other input interfaces 14 and output interfaces.

Reference sign 10*c* designates a, which has a built in display 12 in the form of a touchscreen 13 operating as input interface 14 and output interface at the same time. In addition other peripherals may be connected to the smartphone 10*c*.

Reference sign 10*d* designates a tablet, which also has a built in display 12 formed as a touchscreen 13, therefore this also operates as both an input interface 14 and output interface at the same time. In addition the tablet 10*d* ha a further input interface 14 in the form of a touch pen 15*d*, which enables more precise use of the touchscreen. Naturally further peripherals are also possible here.

At least one processor 16 and storage media 17 are located inside the computers 10 which have been marked schematically with dashed lines in FIG. 1 in the present case the storage media 17 are memories 18. In the case of the desktop PC 10*a* the processor 16 and the memories 18 are arranged in a separate housing 11. It is usual to call the central processor 16 a central processing unit (CPU), the text "CPU" in the text box delimited with dashed lines schematically illustrating the processor 16 makes reference to this. However, the at least one processor 16 may be provided in any known form, for example as a part of a system on chip, which may also have integrated memories 18. This latter component is customarily abbreviated as SoC (system on chip). There may be several processors within one computer 10, an example of this being a so-called multicore processor, which is actually one chip within which the individual cores are also processors 16 themselves.

From the point of view of retaining the data the memories 18 may be of two types: volatile and non-volatile. Non-volatile memory 18 is a storage medium 17 (background storage) that is adapted for permanently storing program codes (programs in short) containing computer commands that may be executed (run) by the processor 16. The very fast access memory 18 actively used by the processor 16 during the running of programs is usually volatile. While the program is being run or as a result of this the computer 10 receives data (for example it reads data via the input interface 14), stores data (temporarily in the volatile memory 18, or long-term in the background storage), processes data and transmits it (such as to an output interface, for example it displays data on the display 12).

Further customary elements may also be in the computer 10 in the way known by a person skilled in the art, such as data buses, switches, connections, etc., which are not separately shown here.

The display 12 of the computer 10 used for the implementation of the present invention is a colour display 12, which means that each of the pixels 20 forming the image dots of the display 12 are made up of several, differently coloured so-called subpixels 21, as illustrated in the enlarged detail of an exemplary display 12 in FIG. 2a, in which the neighbouring subpixels 21 forming one pixel 20 have been framed with a dashed line. The pixels 20 of displays 12 typically contain subpixels 21 in three colours: red, green and blue subpixels 21, which are marked respectively by the letters R, G and B in FIG. 2a. The technology used to display the individual colours depends on the type of display 12, this may take place, for example, using appropriately coloured organic light-emitting diodes (OLED), as in the case of OLED displays 12, or, for example, using controllable liquid crystal filters and white background illumination, as in the case of LCD type displays 12. It should be noted that the use of other display technologies is conceivable, such as QLED or plasma technologies, as is obvious for a person skilled in the art. There are also LCD screens in existence that in addition to the conventional red, green and blue subpixels 21 also contain other coloured subpixels, for example in the Quattron brand LCD screen there is a fourth, yellow coloured subpixel 21 within each of its pixels 20. This is marked with the letter Y in FIG. 2b. In the case of the LCD screens illustrated in FIG. 2c using the so-called PenTile RGBW technology, the fourth subpixel 21 marked with W is controllable to become transparent, in this way it transmits the white background light without it passing through a colour filter, in other words this type of display 12 uses white as the fourth colour.

The calibration test and the colour vision test according to the invention are carried out by a computer program on the computer 10 used by a user. The two types of tests may be implemented with separate computer programs, or within the framework of a single computer program. The computer program(s) may be stored in the non-volatile memory 18 of the computer 10 or they may be read from a separate non-volatile storage medium 17, such as a USB flash drive 19 shown in FIG. 1, which has been indicated beside the desktop computer 10a. The external storage medium 17 may, alternatively, be a CD, DVD, Memory Stick, etc. An embodiment is also conceivable in which the computer program(s) are stored on a remote computer, typically a server, and, for example, the displaying of the given test is realised on the display 12 of the local computer 10 through an Internet connection, and the transmitting of the user input data read through the local input interfaces 14 to the program(s) running on the server for processing also takes place via the Internet.

It is clear for a person skilled in the art that other computers are also conceivable which are different from the computers 10 presented here but which may also be adapted for implementing the methods according to the invention.

Calibration Test

An exemplary embodiment of the calibration method according to the invention is presented using the flow diagram shown in FIG. 3.

During the method a computer 10 is used that has a colour display 12 and at least one input interface 14. A colour vision test for testing the colour vision of a colour blind person is to be displayed on the display 12 of the computer 10 under given ambient lighting conditions, however calibration is required before this takes place in order to be able to take into consideration the effect on colour vision of the colour reproduction capability of the given display 12 and the effect of the given ambient lighting conditions on colour vision, which both influence the colour vision test as explained previously. The given ambient lighting may be natural light (e.g. daylight within a room) or artificial light (e.g. a room illuminated with the light of a lamp). The calibration relates to the performance of the colour vision test under given ambient lighting conditions, therefore it is required that the given ambient light conditions do not change between the time when the calibration test is displayed and when the colour vision test is displayed later. For this in step S10, preferably before the colour vision test is started, a calibration test is displayed on the display 12 in the same ambient lighting conditions for a person with normal colour vision. Preferably, instructions are displayed to perform the calibration test by a user with normal colour vision;

Anyone may be invited to perform the calibration test in the environment of the patient to be tested who knows that they are not colour blind, i.e. anyone who has normal colour vision. If no one in the environment of the patient to be tested knows this for sure about themselves, then it is preferable to invite two female persons to perform the calibration test, as the proportion of females with colour vision deficiency is significantly lower (approx. 0.4%) than in the case of males, therefore the probability that both of the females have colour vision deficiency, and in the same way, is negligible. Apart from this very rare situation, if for example, one person invited to do the calibration test has colour vision deficiency, then from the different results of the two calibration tests it can be determined that at least one of the person has colour vision deficiency, hence the calibration will be unsuccessful and another person or pair of persons will have to be found for the calibration. All this, however, does not make the method according to the present invention unusable, all it means is that the method will be unsuccessful in a very small percentage of cases (if, for example, the results of the calibration tests performed on the two persons are contradictory) or it will lead to an incorrect result (if, for example, persons performing the calibration test who think they have normal colour vision but in fact they have colour vision deficiency). The person with normal colour vision and their selection are not a part of the method according to the invention, in other words step S10 of the method according to the present invention only extends to displaying the calibration test on the display 12, which is designed for a person with normal colour vision, and which, therefore should be performed by a person with normal colour vision. In the following the person participating in the calibration test will be referred to as the user.

During the displaying of the calibration test in step S10, in step S101 preferably an instruction is given to the user (in other words the person with normal colour vision) which when performed ensures that his or her eyes have become adapted to the given ambient lighting conditions. For example, a text instruction is displayed on the display for the user of the calibration test telling the user to look at an object 40 known to him or her to be white, such as a sheet of white paper, for a few minutes, preferably for at least 2 minutes and optimally for 10 minutes. Colour vision is partially a brain signal processing task, therefore in spite of the possible yellowish, bluish, etc. toned light of the ambient illumination, the human brain is able to adjust the white balance, which in practice means that the sensitivity ratios of the S, M and L-cone receptors are tuned so that after a certain time the user sees the colour of an object 40 known to be white as white even though the individual wavelength components measured by an instrument of the light reflected from the object 40 are present in differing intensities, in other words the light reflecting from the object 40 has an objective coloured tone (for example light yellow in a yellowish lamp light).

The instruction for the user may not only be displayed during the calibration test and not only on the display 12. For example, it is conceivable that it has been provided previously as part of the instructions for use, either in electronic or paper form.

It is not possible to guarantee the adaptation of the eyes of the user performing the calibration test to the ambient lighting conditions, but, for example, the probability that the user's eyes have appropriately adapted can be increased with the above instruction, and so the calibration will be more precise. The eyes will still have a degree of adaptation if the user is not asked to perform an exercise that adapts his or her eyes to the ambient lighting conditions, hence the calibration can still be performed, and can be used for ameliorating the colour vision test, but calibration may be less precise from the point of view of taking into account the effect of the ambient lighting conditions on colour vision.

The user is also preferably instructed to maintain and refresh the adaptation of the eyes while performing the calibration test, for example, by returning to look at the white colour (the object 40) for a longer period of time than the amount of time spent looking at the display 12 to prevent the eyes from becoming "disadapted" due to looking at the colours on the display 12 for a long time during the test. If a white sheet of paper or other known white object 40 is not used, instead the automatic adaptation of the eyes to the environment is relied on, it is still preferable to instruct the user to look away from the display 12 and to the environment from time to time while performing the calibration test. Naturally, it is more effective if the user looks at an object 40 he or she knows to be white, because this way adaptation is faster.

During the displaying of the calibration test in step S10, in step S102 a colour determination task is displayed requiring user input in at least one region of the display 12. Henceforward this region will be referred to as "measuring" region. FIG. 4 presents the screen image of an exemplary colour determination task displayed on the display 12. This may be, for example, the screen image of the monitor 12a of the desktop PC 10a. Optional text instructions 32 for the user (marked with a dashed line frame) are displayed on the screen image, preferably in front of the entire background of the measuring region 31, in other words the background of the text instructions 32 is also a part of the measuring region 31. The instructions 32 may also contain instructions relating to eye adaptation, or only the instructions related to the execution of the calibration test.

In the case of this example there are sliders 33 displayed for adjusting the intensity of the red, green and blue subpixels 21. If the display 12 has further coloured subpixels in addition to the red, green and blue subpixels 12, then their intensity is preferably set to 0 for the purposes of performing the colour determination task, and the adjustment of these additional coloured subpixels is not made available to the user. The user is able to change the positions of the sliders 33 via one of the input interfaces 14 of the computer 10 (e.g. the mouse 15a, 15b, 15b' or by using a finger or the touch pen 15d on the touchscreen 13). The colour of the measuring region 31 is adjusted by regulating the intensity of the subpixels 21 in the measuring region 31, preferably according to the actual intensities determined by the sliders 33, therefore the user sees the colour mixed by him or her in the measuring region 31 in real time. Therefore, in this case the user input is the adjustment of the sliders 33, which the user provides as a response to the colour determination task, and which in step S11 is read via one of the input interfaces 14 of the computer 10.

During the performance of an exemplary colour determination task in step S101 the user must set the colour of a white object 44 observed for a prolonged period of time within the measuring region 31 by adjusting the sliders 33, in other words by adjusting the intensity of the red, green and blue subpixels 21. The text instructions 32 displayed on the display 12 may relate to this. Preferably, while setting the colour of the white object 40 the user may also be instructed to take care to look at the object 40 for longer periods of time and at the display 12 for shorter periods of time, so that the illumination of the display 12 has the least possible effect on the degree of adaptation of the eyes. If the user looks at the display 12 for a prolonged time, the degree of adaptation of the eyes to the ambient light will be reduced, and the calibration will be less precise from the point of view of taking into consideration the effect of the ambient lighting conditions.

When setting the white colour of the measuring region 31 it may happen that although the colour of the measuring region 31 is now similar to the colour of the reference white object 40, it is still lighter or darker than that. In order to correct this a further slider 34 is preferably provided with which the brightness of the measuring region 31 may be adjusted. Optionally it may also be made possible to adjust the hue of the display 12 and its saturation as well.

The user input read in step S11 is evaluated in step S12, and as a result of the evaluation the display error resulting from the combination of the colour reproduction capability of the display 12 and the effect of the ambient lighting conditions on colour vision is determined in step S13. It is not intended to separate the effect of the colour reproduction capability of the display 12 on colour vision and the effect of the ambient lighting conditions on colour vision from each other or to determine them separately, as these jointly influence how the user sees the colours appearing on the display 12.

During the evaluation account is preferably taken of the fact that the majority of problems related to colour vision are manifested in mistaking the colours red and green, therefore in the case of the above example the evaluation preferably consists of determining the r and g values of the intensity of the red and green subpixels 21 from the positions of the sliders 33, and optionally of the slider 34, set by the user, which in standard depiction are each a number between 0 and 255, then the difference of these is taken. Furthermore, account may also be taken of the read brightness value br, which refers to how bright the pixels of the display 12 are. In step S13 the result of the evaluation will be the r–g value, which is regarded as the display error resulting from the combination of the colour reproduction capability of the display 12 and the effect of the ambient lighting conditions on colour vision.

Naturally, the colour vision test may be aimed at measuring the very rare colour vision deficiency linked to errors of the S-cone, in this case during calibration the b value relating to the intensity of the blue subpixels 21 is taken into account, and from this, for example, the r–b, or b–g value as display error is determined as well. Optionally the result of the evaluation may also contain the r–g, r–b and b–g values, as the various components of the display error.

In step S14 a modification to the colour vision test is determined from the display error that corrects the colour vision test with respect to the display error.

For example, the result of the calibration test according to the above example is to be used for a colour vision test for measuring red-green colour vision deficiency, in the case of which the patient being tested needs to set the precise colour yellow (i.e. a yellow with no trace of orange or green) by using the sliders 33 regulating the intensity of the red and green subpixels 21 while the intensity of the blue subpixels 21 is reduced to 0 with the slider 33 that regulates the intensity of the blue subpixels 21.

Mainly two things may be determined as the modification to the colour vision test. On the one hand it is possible to determine a modification to the parameters of the colour vision test so as to correct the parameters relating to the intensity of those coloured subpixels 21 that were taken into account in the display error when the colour vision test is displayed on the display 12. In other words, in the case of this example, when the colour vision test is displayed the r–g difference calculated during calibration is added to the value of the intensity of the red subpixels 21 in the interest of correcting the display error, therefore while setting the yellow colour the corrected yellow result is displayed on the display 12 to the tested patient. In this way it is possible to read as the user input the position to which the patient sets the slider 33, and from this a correct diagnosis may be established, because it is in fact the patient's colour vision deficiency that is being measured and not the display error.

On the other hand it is also possible not to modify the displaying of the colour vision test; instead, as a modification to the colour vision test, a modification to the evaluation of the colour vision test is determined that corrects the measurement result obtained with the colour vision test with respect to the display error in terms of the intensity of the coloured subpixels 21 taken into account in the display error during calibration when evaluating the colour vision test. In the case of the present example this means that the r–g difference obtained during calibration is subsequently subtracted from the result belonging to the yellow colour set by the tested patient (i.e. subtracted from an $r_2$ value set for the intensity of the red subpixels 21). As the "result" is a value close to zero (precisely zero in the case of a person with normal vision and an ideal display 12), therefore by subtracting the display error from this result as the correction, the correct diagnosis of the person with colour vision deficiency is established. If the evaluation of the colour vision test is modified instead the displaying of the colour vision test then it is also possible to perform the calibration test after the colour vision test has been performed.

A colour vision test is also a part of a preferred embodiment of the invention. In this case the calibration method is executed before the colour vision test is started under given ambient lighting conditions, then in step S19 the modification determined during the calibration method is carried out, which in accordance with the above may involve the modification of the display parameters of the colour vision test or the modification of the evaluation parameters.

In step S20 the modified colour vision test is displayed on the display 12. In the present example the colour vision test is very similar to the calibration test, therefore, instead of making unnecessary repetitions reference will be made to the details of the calibration test, and if the colour vision test is not in contradiction with it, the description of the calibration test is valid here also.

The result of the calibration may be improved if care is taken to ensure that the tested patient's eyes are also adapted to the same ambient lighting conditions before he or she performs the colour vision test displayed on the display 12. For this, in step S201 during the colour vision test (or optionally before it) instructions are preferably given to ensure the patient's eyes are adapted to the ambient lighting conditions, for example the patient is instructed to look at an object that he or she knows to be white for a few minutes, preferably for at least 2 minutes, optimally for 10 minutes, preferably the same white object 40 that the person with normal colour vision used for the calibration test. Similarly to the calibration method, the instructions ensuring adaptation of the eyes may be given to the patient in another form as well.

In the case of this example in step S20 during the displaying of the colour vision test in step S202 a colour determination task requiring user input for measuring red-green colour vision deficiency is displayed on the display 12 the schematic screen image of which is presented in FIG. 6. In the case of this task the patient needs to set the colour yellow (i.e. a yellow with no trace of orange or green) in the measuring region 31 of the display 12 by using the sliders 33 regulating the intensity of the red and green subpixels 21. An instruction 32 corresponding to this is displayed on the screen (marked with a dashed line frame). During performance of the task the intensity of the blue subpixels 21 is reduced to 0, and in the case of the present embodiment there is no slider 33 with which the user could adjust the colour blue. The intensity of any further coloured subpixels is also set to 0, and it is not made possible for the user to change this. Preferably in this case a separate slider 34 is provided for adjusting brightness.

In this case the user input is the adjustment of the sliders 33 and 34, which in step S21 is read via one of the computer's 10 input interfaces 14.

The user input read in step S21 is evaluated in step S22, and as a result of the evaluation the patient's colour vision is determined in step S23. The latter also includes the type and severity of the colour vision deficiency.

In the case of the presented example the calibration test was different from the colour vision test, however an example is conceivable in the case of which the calibration test is the same as the colour vision test. For example, during the calibration test the task of the person with normal colour vision acting as user is also to mix the colour yellow (preferably after resting his or her eyes on the white reference object 40).

A further possibility illustrated in FIG. 3*a* is that the tested patient is also asked to perform the calibration test, in this way the colour vision test may be simplified. For example, as the completion of the calibration in step S15 the calibration test is also displayed for the tested patient, during which in step S151 the patient is instructed to look at the white reference object 40 that the person with normal colour vision also used for some minutes, optimally for approximately 10 minutes, then in step S152 the patient is also instructed to perform the white setting task described above, and in step S16 the user input relating to the setting of the slider 33 regulating the intensity of the green colour is read, in other words the g value set by the patient, is read. With this g value the colour vision test relating to the setting of the colour yellow is modified in step S17 in such a way that the value of the green subpixels 21 in the measuring region of the displayed colour vision test is set to g, and compared to this the patient has to set the intensity of the red subpixels 21 in such a way as to mix the colour yellow. By fixing the intensity of the colour green it is possible to use approximately the same control range of the display 12 which has non-linear characteristics.

Other types of colour determination tasks may be displayed both during the calibration test and the colour vision test. In the case of the above examples, the task involved either the person with normal colour vision or the tested patient setting a given colour in the measuring region 31 of the display 12 by adjusting the intensities of the various coloured subpixels 21. However, there may be many types of colour determination tasks, the tasks may involve, for example, adjusting the intensity of more or fewer coloured subpixels 21, for example, the user only has to adjust one type of coloured subpixel 21, while the intensities of the other coloured subpixels 21 are set to a specific value for the user. The colour determination task may involve, for example, selecting one or more colour samples from a set of colour samples displayed in the measuring region 31 according to specific instructions (for example, selecting the colour sample that the user sees as being more orange from among two different shades of yellow colour).

FIG. 7 shows an illustration of the screen image of a more complex colour determination task as it appears on the display 12 of a smartphone 10c used as the computer 10. In the case of this example the measurement region 31 consists of three circular surfaces 31a, 31b, 31c, the colour of which may be changed using the slider 33a, 33b, 33c displayed under each of them. The colour yellow needs to be set in the first circular surface 31a by changing the position Y of the first slider 33a. The central position of the slider 33a indicated with a dashed line V1 would result in the colour yellow in the case of an ideal display 12, in this case the intensity of the red subpixels 21 and of the green subpixels 21 within the circular surface 31a are both 255 (on the standard scale of 0-255). The intensity of the blue subpixels 21 is reduced down to 0 within the circular surface 31a at any position of the slider 33a. By moving the slider 33a to the right (towards the terminal position marked by R) as compared to the central position, the intensity of the red subpixels 21 does not change, while the intensity of the green subpixels 21 drops evenly down to 205 within the circular surface 31a, therefore in this case an increasingly orange yellow will appear as the proportion of the intensity of the colour red will be increasingly greater as compared to that of the colour green. By moving the slider 33a to the left (towards the terminal position marked by G) the intensity of the red subpixels 21 drops evenly down to 205, while the intensity of the green subpixels 21 remains constant within the circular surface 31a, therefore in this case an increasingly green shade of yellow will appear as the proportion of the intensity of the colour green becomes increasingly greater as compared to that of the colour red.

The current position Y on the slider 33a is described with a value between ±50, in such a way that the central position marked with a dashed line is viewed as 0, in the right terminal position the intensity of the a red subpixels 21 is 50 more than the intensity of the green subpixels 21, therefore this is viewed as the value +50, while in the left terminal position the intensity of the red subpixels 21 is 50 less than the intensity of the green subpixels 21, and this is viewed as the value −50.

Naturally, sliders 33a could be used on which the intensity of the red and green pixels can be adjusted over the entire scale of 0 to 255, however in the case of a colour vision test displayed on a small sized display 12 (such as the display 12 of a smartphone 10c) this would result in a small movement of the slider 33a causing a significant colour tone change within the circular surface 31a, in other words the patient would not necessarily be able to precisely mix the colour he or she sees as yellow. In order to overcome this problem it is preferred to allow moving of the slider 33 only in the expected range around yellow, this is why in the case of this example the scale between ±50 presented above was chosen. Naturally a scale wider than this may be chosen, for example, moves between the values ±100.

If during the calibration method the adjustment of brightness has also been made possible on the slider 34, then this result may be used to provide more precise measurement in such a way that, for example, the 255-255 value of the red and green colours are reduced in accordance with the value of brightness. For example, 95% was set for brightness by the person with normal colour vision in the calibration test using the slider 34, then correspondingly the 255-255 value is reduced to the value 243-243 (which represents the correction of one of the components of the display error). In this case in the right side terminal position the value of the intensity of the green subpixels 21 will be 193, and in the left side terminal position the value of the intensity of the red subpixels 21 will be 193. Naturally many forms of scaling are conceivable, henceforward, for the sake of simpler illustration, the original example will be used, in other words at the central position marked with the dashed line V1 the intensity of both the red and the green subpixels is 255 within the circular surface 31a, while the intensity of the blue subpixels 21 is 0. If the brightness value set during calibration is also to be taken into account, then according to that described above the intensity corresponding to 255 will be proportionately reduced, and in the examples to be explained in the following this reduced value will be used instead of the maximum value of 255.

Similarly, in the second circular surface 31b the task is to set the colour purple using the second slider 33b, which when in its central position marked with the dashed line V2 the intensity of the blue subpixels 21 and of the red subpixels 21 within the circular surface 31b is 255, while the intensity of the green subpixels 21 in any position of the slider 33b is 0. The slider 33b being in the terminal position marked by B results in a bluish shade of purple, and the slider being in the terminal position marked by R results in a reddish shade of purple in such a way that, analogous to that described above, the scale here runs between the values ±50. The set position on the second slider 33 is marked with P.

In the third circular surface 31c the task is to set the colour turquoise, which in an ideal case is created at the central position marked with the dashed line V3, where the value of both the blue and the red subpixels 21 is set to 225 within the circular surface 31c. In an analogous way to that described above the third slider 33c being in the terminal position marked by B results in a bluish shade of turquoise, while the terminal position marked by G would result in a greenish shade of turquoise within the circular surface 31c, and a value within the scale of ±50 corresponds to an arbitrary position T.

The values belonging to the Y, P and T positions set by the user are referred towith the letters y, p and t, respectively.

In an ideal case a person with normal vision would set the value of 0 on all three sliders, while in the case of persons with protan or deuteran colour vision deficiency the y, p and t values would be set as follows:

Persons with protan colour vision deficiency set the following values
- on the yellow slider y>0
- on the purple (purple) slider p>0
- on the turquoise (turquoise) slider t=0.

Persons with deuteran colour vision deficiency set the following values
- on the yellow slider y<0
- on the purple (purple) slider p=0
- on the turquoise (turquoise) slider t<0.

The numerical magnitude of the "+" and "−" values (0-50) show the severity of the given type of colour vision deficiency.

The type and severity of protan or deuteran colour blindness could be theoretically determined by the position of the yellow slider alone, but the redundancy resulting from the testing of various colours increases the reliability of the measurement.

Makin use of the calibration method in the case of the above colour vision test takes place in the following way.

If the calibration was performed with an A/4 paper sheet, then the $\Delta$=r−g value is available as display error (or as a component of it if, in addition to this, other factors are determined, such as brightness).

This value must be given to the colour vision measuring software as the initial step of the use of the colour vision test (for example the measuring software may ask for this and the patient has to type it in or, for example, the measuring software and the calibration software may communicate with each other, and the calibration software sends the $\Delta$ value to the measuring software straight away).

Taking account of the correction takes place in the following way.

If the correction is applied when displaying, then corrected colours are displayed within the circular surfaces 31a, 31b, 31c for the positions Y, P, T of the sliders 33a, 33b, 33c as follows:

In every position Y of the slider 33a the colour corresponding to the value y'=y+$\Delta$ is displayed in the circular surface 31a. If y'≥0, then the intensity of the red subpixels 21 in the displayed colour is 255, and the intensity of the green subpixels 21 is 255−y', if y'<0, the intensity of the green subpixels 21 in the displayed colour is 255, and the intensity of the red subpixels 21 is 255+y'. The method has been illustrated schematically in FIG. 7a, where the colour corresponding to the value y' is displayed in the circular surface 31a. Here the values y>0 and $\Delta$>0 have been presumed, but naturally either one or both may be negative numbers, from the point of view of the displaying what is significant is whether the sum of the two is positive or negative. If the value y' is greater than +50 or smaller than −50 then in the case of displaying the intensity of the red and green subpixels 21 the rule applied within the scale is continued. If then the value of +50 is exceeded, in other words y'>50, then the intensity of the red subpixels 21 is still set to the value of 255, and the intensity of the green subpixels 21 is reduced to the value of 255−y'. If y'<(−50) then the intensity of the green subpixels 21 is maintained at the value of 255, while the intensity of the red subpixels 21 is set to the value of 255+y', where a negative number smaller than (−50) is added to the value 255, in other words the intensity of the red subpixels 21 will be smaller than 205. With this setting, if the person being tested also has normal colour vision, then with the slider 33a in its central position (y=0) even in spite of the display error he or she will see the colour yellow (neither reddish nor greenish shade of yellow) within the circular surface 31a.

If only those persons with the most common form of colour vision deficiency, i.e. protan and deuteran colour vision deficiency are to be tested, then it is sufficient to correct the displaying of the red and green colours on the sliders 33b and 33c (irrespective of any error in the colour blue).

Similarly to the above, the colour corresponding to the value p'=p+$\Delta$ is displayed within the circular surface 31b for every position P of the slider 33b according to the rules explained in the case of adjusting yellow. In other words with this setting if the person being tested is a person with normal colour vision, then with the slider 33b in its central position (p=0) even in spite of the display error he or she will see the colour purple in the circular surface 31b that has neither a bluish tone nor a reddish tone.

The colour corresponding to the value t'=t+$\Delta$ is displayed within the circular surface 31c for every position T of the slider 33c according to the rules explained in the case of adjusting yellow. With this setting if the person being tested is a person with normal colour vision then with the slider 33c in its central position (t=0) even in spite of the display error he or she will see the colour turquoise in the circular surface 31c that has neither a bluish tone nor a greenish tone.

Using the above method the y, p and t values set by the patient may serve as the basis of a diagnosis as the display error has already been corrected on the display 12 when these values were inputted by the user.

Another possibility is that the displayed colours themselves are not changed during the measurement of colour vision, instead the y, p, t values corresponding to the read positions Y, P, T of the sliders 33a, 33b, 33c, respectively, as measurement results are subsequently modified according to the formulae y'=y−$\Delta$, p'=p−$\Delta$ and t'=t−$\Delta$, and it is these latter values that serve as the basis of the diagnosis. Here the display error $\Delta$ is subtracted from the y, p and t values corresponding to the positions of the sliders 33a, 33b, 33c, as the deviation from the 0 position is partially or completely caused by the display error and not by the colour blindness.

In connection with the calibration method it was mentioned earlier that an embodiment is conceivable in the case of which the r−b and b−g values are also determined as further components of the display error. In this case the formulae p'=p+(r−b) and t'=t+(b−g) may be used for the colours displayed at the P and T positions, or if the display error is not corrected in the case of displaying, then during diagnosis the calculations may be made with the formulae p'=p−(r−b) and t'=t−(b−g). In this way the very rare fault of the S-cone can be measured.

If calibration takes place with the person with normal colour vision performing the same test as the person with colour vision deficiency when performing the calibration, then the $y_2$, $p_2$, $t_2$ values belonging to every single setting made by the person with colour vision deficiency must be corrected with the same $y_1$, $p_1$, $t_1$ values of the person with normal colour vision.

This may take place in two ways as well:

In case the calibration software operates on the same principle as the measuring software but it is distinct therefrom, then the result y1, p1, t1 of the calibration software belonging to the positions Y1, P1, T1 set by the person with normal colour vision are transferred to the measuring software, and instead of displaying the colours corresponding to the values y2, p2 and t2 belonging to the positions Y2, P2 and T2 when the patient sets the colours, the colours corresponding to the values y2'=y2+y1, p2'=p2+y1 and t2'=t2+y1 are displayed within the circular surfaces 31*a*, 31*b*, 31*c* according to the rules described above. With this method the display error has been corrected in the same way as in the previous example by adding the value Δ=r−g, as the position Y1 of the slider 33*a* itself codes an r−g value increasing by increments of one between −50 and +50, since red and green intensities vary according to definite rules, but in such a way that a unit change of y1 always represents a unit change of r−g with the same sign. In this case the basis of the diagnosis are the y2, p2 and t2 values set and actually inputted by the patient.

It is also possible to take into account the intensity of the blue coloured subpixels 21 by using the values of p1 and t1 in the above formulae, in other words y2'=y2+y1, p2'=p2+p1 and t2'=t2+t1.

If, however, the calibration software results y1, p1, t1 of the person with normal colour vision are only recorded, but the calibration results are not used to modify the measuring software, then the final result must be subsequently corrected. If the focus is only on the display errors of the colours red and green, then the following formulae may be used:

$$y=y2-y1$$

$$p=p2-y1$$

$$t=t2-y1$$

if, however, the colour blue is also to be taken into account, then the following formulae may be used:

$$y=y2-y1$$

$$p=p2-p1$$

$$t=t2-t1$$

where y2, p2, t2 are the values measured for the person with colour deficiency, y1, p1, t1 are the settings made by the person with normal colour vision, and the y, p, t values will be the amounts serving as the basis of the diagnosis.

In the above example it was shown how a task for testing colour vision may be provided by mixing two primary colours (subpixel 21 colours). In the present case the task for the user (patient) was to set a third colour formed from a mixture of two primary colours. The task may also involve colour selection instead of colour setting, here these are also jointly referred to as colour determination tasks. The colour determination task may also be performed with the use of more than two primary colours, the task, for example, may be the setting of various colour tones mixed from two or more primary colours, or their differentiation, or placing them in order, etc. In the case of the above example each colour setting task required the setting of one colour tone within the circular surface 31*a*, 31*b* 31*c* belonging to the given task, but other embodiments are conceivable in the case of which, similarly to the Ishihara test, shapes of various colour tones are displayed for each task, such as tiny circular coloured surfaces. It is obvious for a person skilled in the art that such more complex tasks may be derived from the examples presented above.

Colour Discrimination Test

The present invention further relates to a computer implemented method of testing colour vision. According to a preferred embodiment the colour vision test is a colour discrimination test as will be explained in more detail. The colour discrimination test is preferably supplemented by performing the calibration method according to the invention. The calibration test may be one of the aforementioned calibration tests, the results of which may be used as explained previously. Optionally, the calibration test may be the same test as the colour discrimination test, which will be explained in more detail following the disclosure of the colour discrimination test. The colour discrimination test is displayed on the same display 12 of the same computer 10 under the same given ambient lighting conditions as the calibration test.

A preferred embodiment of the colour discrimination test is illustrated in the flow diagram of FIG. 8. The reference numerals of the steps do not imply order of the steps unless specifically stated so or unless this is entailed by the nature of the given steps.

According to a preferred embodiment the test is started by displaying in step 800 instructions on the display 12 of the computer 10, which when followed by the user cause the user's eyes to be adapted to the ambient lighting conditions. These user instructions of step 800 may be displayed when the computer program (e.g. mobile application) containing the colour vision test is launched. For example, a text instruction can be displayed at the start of the test instructing the user to look at an object 40 known to him or her to be white, such as a sheet of white paper, for a few minutes, preferably for at least 2 minutes and optimally for 10 minutes. The instructions preferably contain advice as to what ambient lighting conditions are best suited for performing the colour vision test, preferably advising the user to perform the colour vision test in daylight, out of direct sunlight, for example outdoor or close to a window. The instructions preferably also contain advice relating to the colour setting of the display, for example advising to the user to use the display's default daylight colour settings.

In step 801 a target colour 81 is selected which has a target hue 81*a*, a target brightness 81*b*, and a target saturation 81*c*. The target hue 81*a* and the target saturation 81*c* together may be referred to as target chromaticity 81*d*.

In step 802, which may be performed before, after or parallel with step 801, a test colour 82 is selected, which has a test hue 82*a*, a test brightness 82*b* and a test saturation 82*c*. The test hue 82*a* and the test saturation 82*c* together may be referred to as test chromaticity 82*d*.

The target colour 81 and the test colour 82 are selected such that the target colour and the test colour are pseudo-isochromatic with respect to a selected type of dichromacy.

Dichromacy is the state of having only two types of functioning colour receptors (cone cells) in the eyes. Dichromats can match any colour they see with a mixture of no more than two pure spectral lights. The type of dichromacy depends on which colour receptor is not functioning. If the L-cone is not functioning (or it is shifted to such an extent that it coincides with the spectral sensitivity curve of the M-cones) then the dichromat has protanopia. If the M-cone is not functioning (or it is shifted to such an extent that it coincides with the spectral sensitivity curve of the L-cones) then the dichromat has deuteranopia. If the S-cone is not functioning this results in tritanopia, however, as explained before, this is a very rare and generally not permanent condition.

Pseudo-isochromatic colours only appear isochromatic (having the same hue) to dichromats, these colours appear different to people with normal colour vision. In the context of the present invention the term "pseudo-isochromatic"

signifies colours of different hue which appear to be of identical hue (isochromatic) to dichromats but which appear to be of different hue (non-isochromatic) with respect to normal colour vision, i.e. for test subjects with normal colour vision. As will be explained in more detail later on, certain chromatically different colours may appear isochromatic even to people with normal colour vision as well. For the sake of clarity such colours are not referred to as pseudo-isochromatic colours.

There are various ways to select pseudo-isochromatic colour pairs, for example the Ishihara plates use pseudo-isochromatic colours, however, it is noted that some colours of the Ishihara plates are not reproduceable on a computer display 12 because computer displays 12 are only capable of producing colours of limited chromaticity. Chromaticity is an objective specification of the quality of a colour regardless of its brightness (luminance). Chromaticity consists of two independent parameters referred to as hue and saturation (colourfulness).

Another way of defining that the target colour 81 and the test colour 82 are pseudo-isochromatic colours with respect to the selected type of dichromacy, is that the target colour and the test colour are selected such as to correspond in a chromaticity diagram of a colour space to two colours of different hue located substantially on a common confusion line of the selected type of dichromacy.

In many technical applications, perceivable colours are represented by coordinates in a colour space. Usually, such a space has three dimensions, corresponding to three different properties of colour that are sufficient to uniquely describe each colour. If one of those dimensions correspond to the luminance, determining the perceived brightness, then the remaining two dimensions are interpreted as the chromaticity, defined through two coordinate values, hue and saturation.

For example, the well-known CIE chromaticity diagram may be used, wherein the normalized coordinates x and y are calculated from the XYZ values of CIE XYZ colour space (e.g. the CIE 1931 XYZ colour space, however, other CIE XYZ colour space standard may be used as well). The CIE chromaticity diagram depicted in FIG. 9 may be considered as one plane (for one particular brightness) of the three-dimensional CIE XYZ colour space. The visible chromatic values in this coordinate system form a horseshoe shaped region, with the spectrally pure (monochromatic) colours on the curved boundary.

If the colours of the subpixels 21 of the display 12 are represented in the CIE chromaticity diagram of FIG. 9, these will correspond to three vertices of a triangle and the display 12 can only produce colours within this triangle. Accordingly, the CIE chromaticity diagram can also be used to visualize the colour gamuts (i.e. the ranges of producible colours) for the display 12. FIG. 9 shows two such triangles 91, 92 corresponding to two different types of displays 12. The triangle 91 corresponds to a LED display 12, and the triangle 92 corresponds to the colour space of an sRGB (standard Red Green Blue) display 12, which is often the "default" colour space for images that contain no colour space information, especially if the images' pixels are stored in 8-bit integers per colour channel.

The white points corresponding to black body radiation at different temperatures are located along the so-called Planckian locus 93 as it is well known in the art. The Planckian locus 93 is the path that the colour of an incandescent black body would take in a particular chromaticity space as the black body temperature changes. It goes from deep red at low temperatures through orange, yellowish white, white, and finally bluish white at very high temperatures. The most commonly used white points are the equal energy white point W corresponding to the 6,500 K black body radiation, located at [x, y]=[⅓, ⅓]. and the CIE Standard illuminant D65 white point, illustrated with reference sign C, corresponding to black body radiation of 6,504 K, and also corresponding roughly to the average midday light in Western Europe/Northern Europe (comprising both direct sunlight and the light diffused by a clear sky), hence it is also called a daylight illuminant.

Once the target colour 81 and the test colour 82 have been selected from a common confusion line 94, 95, 96 of the CIE XYZ colour space the coordinates of the colours 81, 82 can be transferred mathematically to RGB coordinates of the given display 12 if the coordinates of the red, green and blue subpixels 21 are known, which define the triangle 91, 92 of the display's 12 colour space within the CIE chromaticity diagram. Accordingly, a preferred embodiment comprises the step of obtaining the type of the display 12 being used and the coordinates of the red, green and blue subpixels 21 of the given display 12. For example, the display's 12 type may be queried or detected automatically or may be inputted by the user via the input interface 14, after which the required coordinates can be obtained from a look-up table containing the coordinates of the red, green and blue subpixels 21 for various types of displays 12. If the type of display 12 cannot be determined or the type is not found in the look-up table, or no such look-up table is available, then the coordinates of the sRGB triangle 92 can be used as a good approximation to obtain the RGB coordinates of the colours 81, 82 selected from the common confusion line 94, 95 or 96. This will introduce some error because the colours displayed on the given display 12 using the obtained RGB coordinates generally do not precisely lie on the selected common confusion line 94, 95 or 96, instead the displayed colours correspond to colour points in the CIE chromaticity diagram, which are only very close to the selected common confusion line 94, 95 or 96. In the context of the present invention the hue of the displayed colours obtained by such a transformation is understood to correspond to the hue 81a and 82a of the target colour 81 and the test colour 82, respectively. The effects of the error introduced by the imperfect transformation can be compensated for by calibration and/or by combining the colour discrimination test with a colour identification test as will be explained later on.

Various other colour space representations are also known in the art wherein a chromaticity diagram can be defined in a plane. For example, the HSL colour space represents the colours in a cylindrical coordinate system, wherein brightness is measured along the axis z, saturation corresponds to the r distance from the z axis and hue corresponds to the angle measured from an axis x. In the HSL space each plane that is perpendicular to the axis z contains a chromaticity diagram of a given brightness. The different colour space representations can be transformed into one another.

Confusion lines are the lines in the chromaticity diagram (e.g. the CIE chromaticity diagram) on which hues are not distinguishable for corresponding dichromats. Each type of dichromat has its confusion lines. FIG. 10a shows the protanope confusion lines 94 (L-cone disfunction, protanopia), FIG. 10b shows the deuteranope confusion lines 95 (M-cone disfunction) and FIG. 10c shows the tritanope confusion lines 96 (S-cone disfunction), wherein additionally the protanope confusion line 94 and the deuteranope confusion line 95 which traverse the white point W have been indicated as well. As can be seen each type of confusion lines 94, 95, 96 intersect in a common point, the so-called co-punctal point.

If the target colour 81 and the test colour 82 lie on (or substantially on) a common confusion line in a chromaticity diagram of a colour space (e.g. in a CIE XYZ chromaticity diagram) this implies that the brightness 82$b$ of the test colour 82 is the same as the target brightness 81$b$. Preferably, the brightness is chosen so that the target colour 81 and the test colour 82 correspond to two points of the CIE XYZ chromaticity diagram on which the brightness is set to approximately 35 to 65%, more preferably to approximately 40 to 60%, for example to approximately 50% whereby the white point W appears as a light shade of grey. This choice is more comfortable for the eye than using CIE XYZ chromaticity diagram at a brightness where the white point W appears white on the screen of the given display 12.

In the CIE XYZ colour space saturation depends on how close the selected colours 81, 82 are to the boundary of the chromaticity diagram, because the saturation is highest along the boundary and decreases towards the white point W.

Preferably, such target colour 81 and test colour 82 are selected which lie on a common confusion line 94, 95, 96 traversing the white point W of the chromaticity diagram. In order to have different hue, the target colour 81 and the test colour 82 are selected so as to be located on opposite sides of the confusion line 94, 95, 96 with respect to the white point W. This is also possible in other colour spaces than the CIE XYZ colour space.

According to a particularly preferred embodiment, the target saturation 81$c$ and the test saturation 82$c$ are equal or close to equal.

If the colour vision test is performed in daylight, then the equal energy white point W corresponding to the 6,500 K black body radiation can be used, which is well suited for measurements performed in day light. The standard white point C of the standard white light, which is approximative sunlight, is an equally good choice for daylight measurements. However, for the purpose of this embodiment, the equal energy white point W will be used.

It is noted, that if the ambient lighting conditions are substantially different from daylight then the result of any one of the calibration tests described above can be used to determine which colour temperature is best suited for the measurement, and in this case the white point corresponding to this colour temperature can be used. This is because the eye adapts to the ambient lighting conditions and if the ambient lighting condition is significantly different from the hypothetical 6,500 K black body radiation then the adapted eye will perceive a slightly different colour as white, whereby the white point is shifted along the Planckian locus. The locations of the actual white point is also influenced by the colour reproduction capability of the display 12, which is automatically taken into account when using the result of the calibration test to define the actual white point.

Preferably, the white point corresponding to the ambient lighting conditions is used, however, if the subject is instructed to perform the colour vision test in daylight then the equal energy white point W corresponding to the 6,500 K black body radiation can be used. If any other point is used in the vicinity of the 6,500 K white point the test may still be sufficiently accurate.

According to the present embodiment, the method is performed in daylight, and the equal energy white point W of the CIE chromaticity diagram is used corresponding to the 6,500 K black body radiation, its coordinates being: $[x,y]=[\frac{1}{3}, \frac{1}{3}]$. As explained above, any other white point (perceived as white by a subject with normal colour vision) can be used within its vicinity, which can be defined e.g. by x, y coordinate pairs for which $[x,y]=[\frac{1}{3}\pm 0.05, \frac{1}{3}\pm 0.05]$.

The confusion line 94, 95, 96 traversing the white point W is divided by the white point W into two halves. One half is on one side of the confusion line with respect to the white point, and the other half is on the other side. If the white point W substantially corresponds to the ambient lighting conditions, then the hue is substantially the same on each side, only the saturation increases as the location of the point moves from the white point to the circumference. However, the hue on one side of the white point W is different from the hue on the other side. This implies that the target colour 81 is selected from one side and the test colour 82 from the other side.

It is also noted that the target colour 81 and the test colour 82 may be located on any confusion line 94, 95, 96 even one that does not traverse the white point W. However, in any case the target hue 81$a$ and the test hue 82 have to be different with respect to normal colour vision in the sense that they are distinguishable by a person with normal colour vision. As is well known in the art even chromatically different colours may appear indistinguishable to people with normal vision. This phenomenon is best described with the MacAdam ellipses 98 schematically illustrated in FIG. 11. A MacAdam ellipse 98 is a region on a chromaticity diagram which contains all colours which are indistinguishable from the colour at the centre of the ellipse 98 by people with normal colour vision. The contour of the ellipse 98 therefore represents the just-noticeable differences of chromaticity.

The target colour 81 and the test colour 82 are chosen to be pseudo-isochromatic, which means by definition that these colours 81, 82 only appear isochromatic with respect to a certain type of dichromacy but these colours 81, 82 have different hues 81$a$, 82$a$ both in a objective sense and with respect to normal colour vision (i.e. the two hues 81$a$, 82$a$ can be discriminated from each other by people with normal colour vision).

For example, the CIE chromaticity diagram of the CIE XYZ colour space is taken as reference (e.g. the CIE 1931 XYZ colour space, however, other CIE XYZ colour space standard may be used as well). The target colour 81 and the test colour 82 is selected from a common confusion line 94, 95, 96 in such a way that the target colour 81 and the test colour 82 are not located within a common MacAdam ellipse 98. For example, if the target colour 81 and the test colour 82 are located along the deuteranope confusion line 95 shown in FIG. 11, the test colour 82 has to lie outside of the MacAdam ellipse 98 (in particular, any MacAdam ellipse 98) containing the target colour 81, otherwise even test subjects with normal colour vision will not be able to distinguish between the two colours 81, 82. Furthermore, both the target colour 81 and the test colour 82 have to be within the triangle 91, 92 defining the display's 12 colour gamut otherwise the colours 81, 82 cannot be produced by the given display 82. It should be appreciated that any other chromaticity diagram may be used since both the confusion lines 94, 95, 96 and the MacAdam ellipses 98 of the CIE chromaticity diagram can be transformed mathematically into any other chromaticity diagram.

Once the target colour 81 and the test colour 82 are selected a target image 83 is provided in step 803 and a plurality of test images 84 are provided in step 804. These images 83, 84 can be provided from a database or can be generated for the test, optionally based on the calibration results (e.g. by determining the actual white point W corresponding to the ambient lightning conditions and the colour reproduction capability of the display 12)

An exemplary target image 83 and exemplary test images 84 are shown in FIG. 12 on a common image background 87. The image background 87 is preferably of neutral colour, meaning low saturation (less than 30%, preferably less than 15%, more preferably close to 0%, most preferably 0%) and moderate brightness (preferably 35-65%, more preferably 45-55%, for example 50%), which is grey. This has for advantage that the colour grey is less likely to cause re-adaptation of the user's eyes from the adaptation obtained from the ambient lighting conditions as the user's gaze wanders on the screen of the display 12.

The target image 83 comprises a set of target marks 85 having a hue corresponding to the target hue 81*a* and having an average brightness corresponding to the target brightness 81*b*. By corresponding it is meant that the hue of the target marks 85 is equal to or substantially equal to the target hue 81*a* and the average brightness is equal to or substantially equal to the target brightness 81*a*. The target marks 85 preferably have a saturation that corresponds to the target saturation 81*c* of the target colour 81, i.e. the saturation of the target marks 85 is equal to or substantially equal to the target saturation 81*c*. This means that the chromaticity of the target marks 85 corresponds to the chromaticity 81*d* of the target colour 81. Alternatively, only the average saturation of the target marks 85 corresponds to the chromaticity 81*d* of the target colour 81.

Preferably, the target marks 85 are blurred disk-like shapes of random diameter and quasi-random brightness located randomly within the target image 83. The disk-like shapes may be disks or forms of other shapes like triangles, squares, stars, etc. Blurred means that the disk-like shape does not have a definite contour, instead the boundary of the shape melts into the common image background 87 as regards hue, saturation and brightness. Optionally the target image 85 may have its own background, which is preferably also of a neutral colour (low saturation and moderate brightness) like the common image background 87, e.g. a different shade of grey. In FIG. 9 the target marks 85 are represented by hatched disks, the direction of the hatching represents the hue, the angle of the hatching represents saturation (a greater angle with respect to horizontal corresponding to a higher saturation) and the density of the hatching represents brightness (more dense hatching corresponding to less brightness). The blurred contour of the target marks 85 is not shown (cannot be shown in this representation).

The diameter of each disk-like shape is understood as the diameter of the smallest circle encompassing the disk-like shape. The random diameters are preferably within a range of +/−50% of an average diameter, i.e. the smallest diameter is 50% less than the average diameter and the greatest diameter is 50% more than the average diameter. A wider or a narrower range may be chosen as well. Preferably, each disk-like shape has such a diameter that when it is viewed centrally (when it is in the centre of view) it is seen under an angle of 10-20 degrees when the display 12 is viewed from a normal distance, the latter signifying the average distance from which users generally view the given type (size) of display 12. Another way of defining the diameters is by pixels. According to a preferred embodiment the average diameter is between 10 to 20 pixels, preferably about 15 pixels, and the diameters of the individual target marks 85 is between 5 to 30 pixels each. A wider or a narrower range may be chosen as well. Preferably, the disk-like shapes may overlap.

The brightness of each target mark 85 is quasi-random meaning that it appears random, however, the average brightness within the target image 83 has a pre-selected value, which is the target brightness 81*b*. According to a preferred embodiment the average brightness is calculated as the mean of the brightness values of each target mark 85. According to another preferred embodiment the average brightness is calculated as the weighted mean of the brightness values wherein the weighting factor is the area of the corresponding target mark 85. The brightness of each target mark 85 is preferably within a range of at least +/−10%, for example approximately +/−30% from the target brightness 81*b*, i.e. the darkest target mark 85 may have a brightness which is 30% less than the target brightness 81*b*, and the lightest target mark 85 may have a brightness which is 30% more than the target brightness 81*b*. A wider or a narrower range or an asymmetric range may be chosen as well. The brightness distribution of the target marks 85 is preferably Gaussian. Keeping the brightness of each target mark 85 of the target image 83 within a limited range is more relaxing for the eyes than if the brightness of the target marks 85 would change very drastically within the target image 83.

At least one target mark 85 is provided within the target image 83, meaning that the set of target marks may 85 consist of a single target mark 85. However, preferably there are more than one target marks 85, preferably there are at least 10, more preferably at least 50 target marks 85.

Each test image 84 comprises a set of test marks 86, which are preferably also formed by blurred disk-like shapes of quasi-random diameter and random brightness located randomly within one of the test images 84. The test marks 86 may lie on the common background 87 or each or some test images 84 may have their own background, which, however, is also of neutral colour e.g. a different shade of grey.

The random diameters of the test marks 86 preferably fall within the same range as the target marks 85 within a range of +/−50% of an average diameter, i.e. the smallest diameter is 50% less than the average diameter and the greatest diameter is 50% more than the average diameter. A wider or a narrower range may be chosen as well. Preferably, each disk-like shape has such a diameter that when it is viewed centrally (when it is in the centre of view) it is seen under an angle of 10-20 degrees when the display 12 is viewed from a normal distance, the latter signifying the average distance from which users generally view the given type (size) of display 12. Another way of defining the diameters is by pixels. According to a preferred embodiment the average diameter is between 10 to 20 pixels, preferably about 15 pixels, and the diameters of the individual target marks 85 is between 5 to 30 pixels each. A wider or a narrower range may be chosen as well. Preferably, the disk-like shapes may overlap.

The brightness of each test mark 86 is quasi-random meaning that it appears random, however, the average brightness within each test image 84 has a pre-selected value. According to a preferred embodiment the average brightness is calculated as the mean of the brightness values of each test mark 86 within a given test image 84. According to another preferred embodiment the average brightness is calculated as the weighted mean of the brightness values wherein the weighting factor is the area of the corresponding test mark 86 within a given test image 84. Furthermore, the brightness of each test mark 86 within a given test image 84 is preferably within a range of at least +/−10%, for example approximately +/−30% from the average brightness of the test marks 86 within the given test image 84. A wider or a narrower range or an asymmetric range may be chosen as well. The brightness distribution of the test marks 86 may be, for example, Gaussian. Keeping the brightness of each test mark 88 of a given test image 84 within a limited range is more relaxing for the eyes than if the brightness of the test marks 86 would change very drastically within the same test image 84.

At least one test mark 86 is provided within each test image 84, meaning that the set of test mark 86 within each test image 84 may consist of a single test mark 86. However, preferably there are more than one test marks 86 within each test image 84, preferably there are at least 10, more preferably at least 50 test marks 86 within each test image 84.

The test images 84 are provided in different hue and brightness as follows.

A first test image 84a is provided, which comprises a set of first test marks 86a having a hue corresponding to the target hue 81a and having an average brightness that is different from the target brightness 81b. The first test marks 86a preferably have a saturation that corresponds to the target saturation 81c of the target colour 81. This means that the chromaticity of the first test marks 86a corresponds to the chromaticity 81d of the target colour 81. Alternatively, only the average saturation of the first test marks 86a corresponds to the chromaticity 81d of the target colour 81.

A second test image 84b consisting of a set of second test marks 86b having a hue corresponding to the test hue 82a and having an average brightness corresponding to the target brightness 81b. The second test marks 86b preferably have a saturation that corresponds to the test saturation 82c of the test colour 82, whereby the chromaticity of the second test marks 86b corresponds to the chromaticity 82d of the test colour 82. Alternatively, only the average saturation of the second test marks 86b corresponds to the chromaticity 82d of the test colour 82.

Any number of third test images 84c may be provided including the possibility of providing zero third test images 84c, but preferably at least one, more preferably at least two, even more preferably at least four third test images 84c are provided in order to decrease the probability of an accidental correct selection as will be explained later on. Each third test image 84c comprises a set of third test marks 86c having a hue corresponding to the test hue 82a and having an average brightness that is different from the target brightness 81b. The third test marks 86c preferably have a saturation that corresponds to the test saturation 82c of the test colour 82, whereby the chromaticity of the third test marks 86c corresponds to the chromaticity 82d of the test colour 82. Alternatively, only the average saturation of the third test marks 86c of each third test image 84a corresponds to the chromaticity 82d of the test colour 82.

It is possible to use further test images 84 (not shown) consisting of further test marks 86 which have a hue and/or saturation differing from that of both the target image 81 and the test image 82, and the average brightness can be of any value.

In step 805 the target image 83 and the test images 84 are displayed such that the target image 83 is displayed in a continuous target region 88 (e.g. a circle) of the display 12 and the plurality of test images 84 are displayed in a plurality of continuous test regions 89 (e.g. a circle) of the display 12 that are distinct from the continuous target region 88 and from each other. Preferably the target region 88 and the test regions 89 are also spaced from each other. Preferably the target region 88 is in the centre and the test regions 89 are located around the target region 88 such as to be equally spaced from the target region 88 and from each other. The first, second and third test images 84a, 84b, 84c are preferably arranged randomly within the plurality of test regions 89 (one test image 84 in each test region 89).

By displaying the target and test images 83, 84 in such a manner the target and test marks 85, 86 having different hues 81a, 82a and substantially different brightness are separated from each other, thus there are no abrupt transitions in either in hue or in brightness between the marks 85, 86 which are closely packed (arranged within the same image 83, 84). Consequently, the displayed test of the present invention does not have a disturbing vibrating effect like the Ishihara-type tests. Furthermore, the neutral (preferably grey) background 87 helps to smooth the varying nerve stimuli generated by the changes in hue and brightness as the user's gaze wanders from one image 83, 84 to another. These measures all have for effect that the chance of provoking an epileptic seizure is reduced as compared to the conventional Ishihara-type tests.

In step 806 instructions (in particular text instructions) are displayed for instructing a user (the test subject) to select one of the plurality of test images 84 based on which has the highest similarity of hue compared to the target image 83. Preferably, the user is instructed to disregard any differences of brightness and/or saturation. Step 806 may precede step 805, or the target image 83, the test images 84 and the user instructions may be displayed in parallel. It is also possible to display the user instructions relating to the colour discrimination task together with the user instructions relating to the adaptation of the user's eyes, whereby step 800 and step 806 are not necessarily distinct from each other.

The image selection may be carried out in any known way using one of the user input interfaces 14, e.g. by allowing the user to select one of the test images 84 by tapping on the corresponding test region 89 of a touchscreen 13, or by allowing the user to select one of the test images 84 by clicking on it with a mouse 15a, 15b, 15b', etc.

In step 807 the user input relating to the selection of a selected test image 84 is read in through the input interface 14 of the computer 10.

In step 808 the test is evaluated based on the user's selection such that if the selected test image 84 corresponds to the first test image 84a then determining a correct selection, and if the selected test image 84 corresponds to one of the second or third test images 84a, 84b then determining an incorrect selection. An incorrect selection generally indicates a disorder of a type of cone affected by the selected type of dichromacy. For example, if the selected type of dichromacy is protanopia then the affected cone is the L-cone and the colour vision deficiency is related to the disorder of the L-cone. Generally, this means protanomaly, in rare cases the disorder may by protanopia (which may be regarded as the extreme condition of protanomaly). It is noted that if a determination of correct selection is made, this is understood to refer to the performed test, it means that the test subject (user) can distinguish between the target colour 81 and the test colour 82, whereby the test subject has normal colour vision with respect to these two colours 81, 82. This does not mean normal colour vision in an absolute sense. The user may have other type of colour vision anomaly (e.g. deuteranomaly or in very rare cases tritanomaly if protanomaly was being tested), or the user may have less severe colour vision deficiency (e.g. protanomaly if this was being tested), which did not show up with the selected target colour 81 and test colour 82, but which may be detected with another pair of target colour 81 and test colour 82. It is further noted that statistically there is a chance that the user selects the first test image 84a by chance (i.e. without actually being able to distinguish between the target hue 81a and the test hue 82a) This statistical error is substantially reduced by the application of the second test image 84b because people with colour deficiency tend to distinguish between the colours they confuse by relying on brightness. In this way the second test image 84b having the same average brightness as the target image 83 will seem more similar to the target image 83 for a user with the given type of colour vision deficiency than the first test image 84a, which has a different average brightness.

The step 808 of evaluation may be carried out by the computer 10 on which the test is being performed, or the test results may be sent to a remote computer (e.g. a server) via a data communication channel established over the Internet or other communication network (e.g. GSM), and step 808 is performed by a software running on the remote computer. In the context of the present invention the remote computer may be provided in the form of a cloud server and step 808 may be carried out by any one or more of the computers constituting the cloud server.

The severity of the colour vision deficiency may be determined based on the distance of the target colour 81 and the test colour 82 measured along their common confusion line 94, 95 or 96 (target colour 81 and the test colour 82 have been selected such as to lie substantially on a common confusion line 94, 95 or 96). The distance is indicative of a certain severity. A severe condition of colour vision deficiency means that the user cannot distinguish even between colours 81, 82 that lie far apart from each other on their common confusion line 94, 95 or 96. A mild condition would be indicated by the fact that the user can correctly identify the first test image 84a if the distance of the target colour 81 and the test colour 82 is big (thus a correct selection is made for this pair of colours 81, 82, signifying normal vision), but the user selects the second image 84b or one of the third images 84c if the distance of the target colour 81 and the test colour 82 is small, which is an incorrect selection for these two colours 81, 82 and indicative of a colour vision deficiency.

Accordingly, in order to determine the severity of the colour vision deficiency preferably a plurality of tests are conducted with the same user (test subject).

According to a preferred embodiment this is done by repeating the above described steps with a plurality of pairs 80 of target colour 81 and test colour 82 of which colour pairs 80 three are illustrated in FIG. 13. In the present embodiment all the colour pairs 80 are selected such that the target colour 81 and the test colour 82 both lie on the protanope confusion line 94 traversing the white point W. Some target colours 81 are selected so as to lie on one side of the confusion line 94 with respect to the white point W while other target colours 81 are selected to lie on the other side of the confusion line 94 with respect to the white point W. The test colours 82 of each pair 80 are selected from the opposite side as the target colour 81 of the given pair 80 whereby the test hue 82a is always different from the target hue 81a. Preferably, the test colours 82 of each pair 80 are selected with similar test saturation 82c as the target saturation 81c of the corresponding target colour 81. As can be seen the distance of the target colour 81 and the test colour 82 measured along their common confusion line 94 are different for each depicted colour pair 80. This distance is referred to as colour distance. In the present embodiment the colour distance is determined by the target saturation 81c and the test saturation 82c, the higher these two saturations 81c, 82c, the greater the colour distance. (This would not necessarily be the case if other protanope confusion lines 94 were used.)

The test is repeated with the plurality of colour pairs 81, 82, such that a new target image 83, new first test image 84a, new second test image 84b and any number of new third test images 84c are provided in each test based on the given target colour 81 and test colour 82. It is noted that when repeating the test step 806 of displaying user instructions may be performed only once, for example at the start of the first test in the test series. According to another preferred embodiment the user instructions are displayed permanently while the images 83, 84 are changed for each test.

In order to increase the reliability of the tests, the same colour pairs 80 can be used to generate more than one tests, whereby more than one tests have the same colour distance between their target colour 81 and test colour 82. The consecutive pairs of target colour 81 and test colour 82 of each test may be of increasing colour distance along the common protanope confusion line 94, or the order of the tests may follow any other rule or may be random with respect to the distances between the target colour 81 and test colour 82 of the colour pairs. The images 83, 84a, 84b, 84c are displayed and the user is prompted to chose from the test images 84 based on similarity of hue with the given target image 83.

The plurality of tests is evaluated based on all correct and incorrect user selections, a correct selection being a selection wherein the first test image 84a is selected by the user, every other selection being an incorrect selection. The severity of the colour vision deficiency (in this case protanomaly) may be established based on the number of incorrect selections (possibly taking into account the correct selections as well) because a user having protanomaly of a certain severity will confuse the hues under a critical colour distance, hence all tests applying a colour pair 80 with a colour distance below this critical colour distance would result in incorrect selections with a statistically low but non-zero probability of some correct selections as well. It is noted that a correct selection may be the result of pure luck, meaning that the user does not see the difference of hue, instead simply guesses from the six possible answers (if four third test images 84c are displayed). There are many ways to eliminate this risk, one being the application of the second test image 84b having the same average brightness as the target image 83. Another way of reducing the probability of an accidental correct selection is to increase the number of tests, including the possibility of providing more than one tests with the same colour distance.

Preferably, the severity of the colour vision deficiency (in this case protanomaly) is categorized as mild, moderate and sever based on the number of incorrect answers thresholds being provided for each category. For example in test series consisting of twenty tests for testing protanomaly wherein the applied colour distances vary evenly within the range starting with the minimal colour distance that is distinguishable by people with normal colour vision (corresponding to the width of the MacAdam ellipse 29 at the selected white point W) and the maximum colour distance possible along the given confusion line 94 (corresponding to the maximum saturation for both the target colour 81 and the test colour 82), the thresholds may be defined such that 3 to 8 incorrect selections is categorized as mild protanomaly, 9 to 14 incorrect selections is categorized as moderate protanomaly and 15 to 20 incorrect selections is categorized as severe protanomaly. It would be equally possible to base the categorization on the proportion of incorrect and correct selections.

The severity of the colour vision deficiency may be obtained as a more complex function of the number of incorrect selections. In particular, the severity of the colour vision deficiency could be determined by taking into account the distances of the target colour 81 and the test colour 82 of those colour pairs 80 for which an incorrect selection was made. For example, the plurality of tests could be evaluated based on a weighted percentage of the incorrect user selections, the weighting factor corresponding to the colour distance of the target colour 81 and the test colour 82 of the respective colour pair 80.

The above described test series may be performed with colour pairs 80 selected such as to lie along the deuteranope confusion line 95 traversing the white point Was illustrated in FIG. 14. This test series results in determining whether or not the user has deuteranomaly.

Similarly, one of the tritanope confusion lines 96 could be used in the test series.

More than one type of colour vision deficiency may also be tested in a test series. According to a preferred embodiment a first group of plurality of pairs 80 of target colour 81 and test colour 82 are selected such that the common confusion line is the protanope confusion line 84 and selecting a second group of plurality of pairs 80 of target colour 81 and test colour 82 such that the common confusion line is a deuteranope confusion line 95. The test is repeated with the first group of plurality of colour pairs 80 and with the second group of plurality of colour pairs 80. The plurality of tests are evaluated based on the number of the incorrect user selections within the first group of colour pairs 80 and within the second group of colour pairs 80. A colour vision deficiency relating to a disorder of L-cones is determined if the number of the incorrect user selections within the first group exceeds the number of incorrect user selections within the second group by a given first threshold; and a colour vision deficiency relating to a disorder of M-cones is determined if the number of incorrect user selections within the second group exceeds the number of incorrect user selections within the first group by a given second threshold. The first and second thresholds can be determined from calibration with a user having normal colour vision as will be explained later on. In absence of calibration both the first and second threshold is at least one, preferably 2 to 3.

According to a further preferred embodiment a third group of a plurality of pairs 80 of target colour 81 and test colour 82 are selected such that the common confusion line is the tritanope confusion line 96, e.g. the one depicted in FIG. 10c traversing the white point W. The test is repeated with the third group of plurality of colour pairs 80 and the plurality of tests are evaluated in the third group by determining the number of the incorrect user selections in the third group. The number of the incorrect user selections in the third group is preferably used to calibrate the evaluation of the plurality of tests in the first and second groups. Since a colour vision deficiency of the S-cones is extremely rare, the number of incorrect responses are indicative of the user's general sensitivity of colour differences. Referring back to FIG. 11, the MacAdam ellipses 98 depicted therein have been determined for average colour vision, however, the MacAdam ellipses 98 of each person may vary from the average based on his or her individual skill to discriminate between colours. Therefore, incorrect selections in the third group indicate that the user is less capable of differentiating between different colours than the average people and the results obtained for the first and second groups can be corrected with this information. For example the number of incorrect selections in the third group is subtracted from the number of incorrect selections in the first group and from the number of incorrect selections in the second group If however, it is found that the number of incorrect selections in the third group exceeds the number of incorrect selections in the first and second groups then this may be indicative of the very rare colour vision deficiency related to the S-cones (tritanomaly).

The above described colour discrimination test can be used for calibration purposes as well. When performing the colour discrimination test as a calibration test at least one, preferably two people with normal colour vision are invited to perform (one after the other) the colour discrimination test on the same display 12 which is to be used for testing the subject with colour vision deficiency and under the same ambient lighting conditions, which is preferably daylight (outdoor out of direct sunlight, or indoor close to a window but out of direct sunlight). The calibration test may be performed before or after the test subject has performed the colour discrimination test. The calibration test is preferably started with displaying instructions on the display 12 which when followed by the user(s) will ensure these conditions. Preferably instructions are also displayed, which when followed by the user(s) will ensure adaptation of the eye to the ambient lighting conditions as explained earlier.

If a single test is performed, i.e. a single colour pair 80 is selected then a selection made by the user performing the calibration test is used to validate the test itself: if the user having normal colour vision makes an incorrect selection then the test is preferably discarded because an incorrect selection is not indicative of any colour vision deficiency.

If a series of tests are performed the number of incorrect selections within each group (corresponding to the protanope, deuteranope and tritanope confusion lines 94, 95 or 96) made by the user performing the calibration is preferably subtracted from the number of incorrect selections made by the subject of the colour vision test in the corresponding group. Accordingly, if the user performing the calibration test makes number NP of incorrect selections in the first (protan) group, number ND of incorrect selections in the second (deutan) group and number NT of incorrect selections in the third (tritan) group then these numbers can be used to normalise the test results of the subject of the colour vision test, i.e. the number P, D, T of incorrect selections in the first (protan), the second (deutan) and third (tritan) group, respectively. If the test subject made less incorrect selections in the corresponding group than the calibrating user then the number of incorrect selections can be regarded as being zero. With these rules the normalised numbers P', D' and T' of incorrect selections of the test subject are:

P'=P−NP if P>NP, else P'=0,
D'=D−ND if D>ND, else D'=0,
T'=T−NT if T>NT, else T'=0.

This normalisation can influence the determined severity of the colour vision deficiency, since the number of incorrect selections made by the test subject are decreased in order to compensate for incorrect selections that are not due to colour vision deficiency. It is also possible to not display those tests for which the user with normal colour vision made an incorrect selection.

Preferably a threshold is set for the normalised numbers P', D' and T' of incorrect selections of the test subject and colour vision deficiency is diagnosed only if one of the normalised numbers P', D' and T' exceeds this threshold (e.g. 2) and the type of colour vision deficiency (L-cone, M-cone or S-cone related colour vision deficiency) is determined based on which normalised number P', D' or T' is highest. Another threshold may be set to determine a minimum difference between the highest normalised number P', D' or T' and the second highest normalised number, e.g. a difference of 2 is required to establish the type of colour vision deficiency. Optionally a different threshold difference may be set for each type of colour vision deficiency, e.g. the normalised number P' of incorrect selections in the first (protan) group must exceed the normalised numbers D', T' of incorrect selections in the second and third groups by a first threshold and the normalised number D' of incorrect selections in the second (deutan) group must exceed the normalised numbers P' and T' of incorrect selections in the first and third groups by a second threshold. Similarly, thresholds for the critical number of incorrect selections and the critical differences between each groups can be determined for the case where no calibration is performed.

It is noted, that the numbers NP, ND, NT of incorrect selections made by a user with normal colour vision are expected to be close to zero and close to equal if the colour pairs 80 are chosen to be outside of any common MacAdam ellipse. If this is not the case then a higher number of incorrect selections during calibration (e.g. more than 2 in each group), or a higher difference of incorrect selections between the different groups during the calibration (e.g. a difference of more than 2) generally indicates poor ambient lighting conditions or poor colour reproduction capability of the display 12 or a colour deficiency of the user who is performing the calibration and who is supposed to have normal colour vision.

Consequently, it is possible to determine a critical number of incorrect selections (e.g. 2 out of 60 tests) and a critical difference of incorrect selections between the different groups (e.g. a difference of 2) for the purpose of calibration as well, such that if the number of incorrect selections or the number of difference exceeds the pre-determined critical numbers then this indicates that either the user does not have normal colour vision, or the colour reproduction capability of the display 12 is too poor, or the ambient lighting conditions are unsuitable for colour vision measurement. In this case the calibration test results are preferably discarded and the possible sources of errors are displayed to the user.

According to another preferred embodiment the test series are provided in all three groups (protan, deutan, tritan) and the number T of incorrect selections made in the third (tritan) group of tests by the subject of the colour vision test is used for calibrating the measurement in the first and second groups (protan, deutan), for example by subtracting the number T of incorrect selections in the third group both from the number P of incorrect selections in the first (protan) group and from the number D of incorrect selections in the second (deutan) group. This type of calibration can be applied in addition or instead of the calibration performed by a user with normal colour vision. The reason for this is that practically any test subject can be regarded as having normal colour vision with respect to the third group of tests (tritan), since any degree of tritanomaly is extremely rare.

As explained before the measurement results may have some error due to imprecise transformation of the R, G, B values of the red, green, blue subpixels 21 from the target colour 81 and the test colour 82 that are selected from a common confusion line 94, 95, 96 of a chromaticity diagram. This error is generally amplified the further the selected colours 81, 82 lie from the white point. Consequently, an error, which is attributable to imprecise coordinate transformation may make it difficult to differentiate between severe and moderate cases of colour vision deficiency. It is noted that other factors can contribute to a certain level of uncertainty in differentiating between the severe and moderate cases. This can be ameliorated by the application of the following colour identification test, which is specifically designed to detect severe cases of colour vision deficiency.

The colour discrimination test is implemented in the form of one or more computer programs. The computer program is a software containing computer instructions which when executed by the processor 16 of the computer 10 cause the computer 10 to carry out some or all steps of the colour discrimination test. Since the term "computer" is defined in a broad sense, the term "computer program" also includes various software, e.g. desktop computer programs, tablet and smart phone applications, etc.

The computer program may be a dedicated software or it may be a web application (e.g. a JAVA script application) run by a web browser of the computer 10. According to a preferred embodiment only the steps preceding the evaluation of the test are carried out by the computer program running on the computer 10 of the user, the step of evaluating the test is carried out by a separate computer running on a remote computer 10 (e.g. a remote server or a cloud server).

The invention further relates to the computer 10 which stores such a computer program in its non-volatile storage medium 17.

Colour Identification Test

The present invention further relates to a computer implemented method of testing colour vision by a colour identification test. The colour identification test is preferably supplemented by performing the calibration test according to the invention. The calibration test may be one of the aforementioned calibration tests illustrated on FIG. 3 to FIG. 7a, the results of which may be used as explained previously. According to a preferred embodiment, the calibration test is the same test as the colour identification test, which will be explained in more detail following the disclosure of the colour identification test. If a calibration test supplements the colour identification test then the colour identification test is displayed on the same display 12 of the same computer 10 under the same given ambient lighting conditions as the calibration test.

The colour identification test will now be explained with reference to FIGS. 15 to 16.

A preferred embodiment of the colour identification test is illustrated in the flow diagram of FIG. 15. The reference numerals of the steps do not imply order of the steps unless specifically stated so or unless this is entailed by the nature of the given steps.

According to a preferred embodiment before or at the start of the colour identification test one or more instructions are displayed which, when carried out by the user, ensure that the user's eyes become adapted to the given ambient lighting conditions as explained in connection with the calibration test. For example, a text instruction can be displayed at the start of the test instructing the user to look at an object 40 known to him or her to be white, such as a sheet of white paper, for a few minutes, preferably for at least 2 minutes and optimally for 10 minutes.

According to a preferred embodiment the test is started by displaying in step 900 instructions on the display 12 of the computer 10, which when followed by the user cause the user's eyes to be adapted to the ambient lighting conditions. The user instructions of step 900 may be displayed when the computer program (e.g. mobile application) containing the colour identification test is launched. For example, a text instruction can be displayed at the start of the colour identification test instructing the user to look at an object 40 known to him or her to be white, such as a sheet of white paper, for a few minutes, preferably for at least 2 minutes and optimally for 10 minutes. The instructions preferably contain advice as to what ambient lighting conditions are best suited for performing the colour identification test, preferably advising the user to perform the colour identification test in daylight, out of direct sunlight, for example outside or close to a window. The instructions preferably also contain advice relating to the colour setting of the display, for example advising to the user to use the display's default daylight colour settings.

A plurality of colour samples 101 are provided in step 901, each colour sample 101 being within the colour gamut of the display 12 and having a hue between 0 to 220. In practice the colour samples 101 are provided by selecting the properties of the colour samples 101, such as hue, saturation and brightness, or the intensity values of the subpixels 21 of the pixels 20 of the given display 12. It is noted that the hue is also defined by the intensity values of the subpixels 21 relative to each other and corresponds to a dominant wavelength when displayed.

The colour samples 101 may, for example, be generated by the computer 10 or the colour samples may, for example, be stored and retrieved from a database.

In step 902 the plurality of colour samples is displayed on the display 12 of the computer 10 by setting the hue, saturation and brightness, corresponding to setting the intensity values of the subpixels 21 of the pixels 20 of the display 12, so as to obtain the colour of each colour sample 101. The intensity values of the subpixels 21 of the pixels 20 making up the colour sample 101 are set such that the hue of the colour sample 101 has a value between 0 to 220 on the standard scale of 0 to 255. It is noted that the hue is often represented in degrees from 0 to 360 degrees, in this representation preferably only the hues between 0 to 310 degrees are used because the hue range between 310 and 360 degrees has no equivalent in visible spectrum, it can only be simulated by mixing high frequency light (blue or violet) with red light, which results in something between magenta and red on the purple-line. In the context of the present invention whenever the hue is given as a number and not as a degree, the value is understood to relate to the hue scale of 0 to 255.

The brightness of each colour sample 101 is preferably between 25-75%, more preferably between 40-60%, and the saturation is preferably between 25-90%, more preferably between 40-80%. The difficulty of the colour identification test can be increased by decreasing the saturation. The difficulty level also increases if the brightness is increased above 75% or decreased below 25%. It is noted that the saturation and the brightness may also be represented on a scale of 0 to 255, in which case the value of the saturation and the brightness is the above given percentage times 256 minus 1.

The colour samples 101, when displayed, may have any shape. FIG. 16 schematically illustrates an exemplary screen shot of the display 12 wherein a colour sample 101 is displayed as a disk-shaped region against a neutral background 100, meaning low saturation (close to zero, preferably less than 30%, more preferably less than 15%) and moderate brightness (preferably 35-65%, more preferably 45-55%, for example 50%), appearing as a light shade of grey. This has for advantage that the colour grey is less likely to cause re-adaptation of the user's eyes from the adaptation obtained from the ambient lighting conditions as the user's gaze wanders on the screen of the display 12. Preferably, the location of each colour sample 101 on the neutral background 100 is selected randomly. This helps to reduce negative effects of any afterimage of the previously displayed colour sample 101, because on the one hand the subsequent colour sample 101 is displayed at a different (random) location and on the other hand the user's gaze has to wander on the neutral background 100 from the location of the previous colour sample 101 to the location of the subsequent colour sample 101, which helps to neutralise the afterimage.

A set of identifiers 102 corresponding to different colours (hues) are also displayed in step 902. Preferably, the set includes identifiers 102 corresponding to the colours "purple", "blue", "turquoise", "white", "green", "yellow", "orange" and "red" The identifiers 102 may actually be the colour names "purple", "blue", "turquoise", "white", "green", "yellow", "orange" and "red". It should be appreciated that the colour names may be in any suitable language, e.g. a language selected by the user. The identifiers 102 may correspond to the colours in other ways, for example the identifiers 102 may be abbreviations of the names of the colours "purple", "blue", "turquoise", "white", "green", "yellow", "orange" and "red", for example "P", "B", "T", "W", "G", "Y", "O" and "R" could stand for "purple", "blue", "turquoise", "white", "green", "yellow", "orange" and "red", respectively, as indicated in FIG. 16. The identifiers 102 may correspond to the given colours in other ways as well. In the context of the present invention the displayed identifier 102 may appear in non-textual form, for example the identifiers 102 may be in the form of signs or images indicating objects which are commonly associated with the colours "purple", "blue", "turquoise", "white", "green", "yellow", "orange" and "red". For example, the image of an aubergine may be used in relation with the colour "purple", the image of water may be used in relation with the colour "blue", the image of a turquoise (mineral) for the colour "turquoise", the image of a snow man may be used for "white", the image of grass for the colour "green", the image of an orange for the colour "orange", the image of fire for the colour "red". Other colour names may be displayed additionally, e.g. "black", "grey". According to a preferred embodiment only the names of pure colours are displayed, meaning that no mixed colour names are displayed (i.e. no colour names formed with the "ish" suffix, such as "greenish yellow"). However, the difficulty of the test can be increased if the names of mixed colours are displayed as well. In this case the mixed colours are preferably taken into account as the colour following the "ish" suffix, for example "greenish yellow" would be taken into account as "yellow".

In step 903 an instruction 103 is displayed instructing a user to select for each colour sample 101 one identifier 102 from the set of identifiers corresponding to the colour (hue) of the colour sample 101. It is noted that hue is the colour appearance parameter of a colour, whereby the set of names can be regarded as corresponding to hues or they can equally be regarded as corresponding to colours. Most users identify the hue (i.e. the colour appearance parameter) with the colour itself, therefore, in order to render the instruction 103 more comprehensive, it may refer to selecting a "colour" instead of "hue". Accordingly, the terms "colour" and "hue" are used as synonyms in the description whenever it is clear that only the colour appearance property of the colour is relevant. The instruction 103 may be displayed together with the colour samples 101 and the identifiers 102 as shown in FIG. 16, or the instruction 103 may appear separately, for example before any colour sample 101 is displayed, i.e. preceding step 902.

The colour sample(s) 101, the identifiers 102 and the instructions are preferably all displayed on the neutral background 100.

More than one colour samples 101 may be displayed at the same time, however, preferably the colour samples 101 are displayed individually, one at a time as shown in FIG. 16, whereby the user has no comparison when selecting a corresponding identifier 102, which makes the task more difficult for users having colour vision deficiency.

If a single colour sample 101 is displayed (as shown in FIG. 16) the user is allowed to select one of the displayed identifiers 102 via the input interface 14, which selection is read in in step 904 after which the subsequent colour sample 101 is displayed. Preferably, the colour samples 101 are displayed in random or quasi-random order with respect to their hues, meaning that the hues of the colour samples 101 are not in an increasing or decreasing order as they appear. It is also possible to allow the user to skip a colour sample 101 for the case that the user is unable to identify its colour (hue).

If more than one colour samples 101 are displayed simultaneously, it is preferred to allow selection of each colour sample 101 by the user input interface 14 or to select one of the displayed colour samples 101 automatically in order to allow the user to select one of displayed identifiers 102 for the selected colour sample 101. After the identifier 102 has been selected a subsequent colour sample 101 is selected automatically or by the user. When all the displayed colour samples 101 have been selected and a corresponding identifier 102 has been selected by the user, a new image is displayed containing colour samples 101 which have not been previously shown (if any).

In step 906 the colour identification test is evaluated. This may be carried out on the same computer 10 where the test is performed, or the obtained data relating to the user selections may be transmitted to a remote computer via any conventional data communication channel established over the Internet or other communication network (e.g. GSM), in which case step 808 is performed by a software running on the remote computer. In the context of the present invention the remote computer may be provided in the form of a cloud and step 808 may be carried out by any one or more of the computers constituting the cloud.

The evaluation of the test includes determining whether any diagnostically important selections have been made by the user. The term "diagnostically important selection" is used herein to refer to a selection wherein:

the identifier 102 corresponding to the colour "orange" or the colour "red" is selected for a displayed colour sample 101 having a hue value between 60 to 220, or the identifier 102 corresponding to the colour "green" is selected for a colour sample 101 having a hue value between 0 to 35, or the identifier 102 corresponding to the colour "white" is selected for a colour sample 101 having a hue value between 105 to 150, or the identifier 102 corresponding to the colour "purple" is selected for a colour sample 101 having a hue value between 105 to 135, or the identifier 102 corresponding to the colour "turquoise" is selected for a colour sample 101 having a hue value between 190 to 220.

The number of diagnostically important selections may be used to determine whether or not the user has a condition of severe colour vision deficiency, which is a condition close to anopia or in extreme cases anopia. The type of anopia can be any type, i.e. protanopia, deuteranopia or tritanopia. For the purpose of determining severe colour vision deficiency it is generally sufficient to identify at least one diagnostically important selection.

It is also possible to test the user within just one or a few hue bands where it is more likely that a user with severe colour vision deficiency will make a diagnostically important selection. The hue bands of interest are preferably selected as follows:

a first hue band of interest is located between 60 to 105,
a second hue band of interest is located between 0 to 35,
a third hue band of interest is located between 105 to 135, and
a fourth hue band of interest is located between 190 to 220.

One or more of these hue bands of interest may be used for selecting the hue of each colour sample 101. It is also possible to use other hues outside of these hue bands as the hues of further colour samples 101.

Preferably at least two, more preferably at least three colour samples 101 are provided within each hue band of interest for the purpose of performing the colour identification test, such that the at least two, more preferably at least three colour samples' 101 hues divide the given hue band into band portions of equal bandwidth such that each band portion contains the hue of one of the selected colour samples 101. This means that if two colour samples 101 are provided within a given hue band then one of the two colour samples 101 has a hue that is located in a band portion corresponding to the first half of the given hue band, and the other one of the two colour samples 101 has a hue that is located in a band portion corresponding to the second half of the given hue band. In case of three colour samples 101 the hues of the colour samples 101 are located in the first third, the second third and the third third of the given hue band, respectively. It is noted that this provision does not exclude the presence of further colour samples 101 within the same band portion. For example, a fourth colour sample having a hue that is also located in the first third of the given hue band. It is also possible to provide more than one colour samples 101 that have the same hue.

Preferably at least 5, more preferably 5 to 15 first colour samples 101 are provided each having a hue selected from the first hue band such that the first hue band is divided into at least five first band portions of equal bandwidth and each first band portion contains at least one selected hue.

Preferably at least 5, more preferably 5 to 15 second colour samples 101 are provided each having a hue selected from the second hue band such that the second hue band is divided into at least five second band portions of equal bandwidth and each second band portion contains at least one selected hue.

Preferably at least 3, more preferably 4 to 10 third colour samples 101 are provided each having a dominant wavelength selected from the third hue band such that the third hue band is divided into at least three second band portions of equal bandwidth and each third band portion contains at least one selected dominant wavelength.

Preferably at least 3, more preferably 4 to 10 fourth colour samples 101 are provided each having a hue selected from the fourth hue band such that the fourth hue band is divided into at least three second band portions of equal bandwidth and each fourth band portion contains at least one selected hue.

According to a preferred embodiment the colour samples are not provided with an even sampling rate along the whole of the visible spectrum, instead the sampling rate is increased within the hue bands of the visible spectrum where it is more likely that a user with severe colour vision deficiency will make a diagnostically important selection. Here, the colour samples 101 (i.e. their respective hues) are selected more densely, meaning higher colour sample number per units of hue. It is also possible to increase the sampling rate by providing multiple colour samples 101 having the same dominant wavelength. Preferably, the sampling rate is higher between hue values of 60 to 100 and 20 to 35 than the average sampling rate over the measuring range.

For example, a normal sampling rate of 1 sample per 10 units of hue can be used between the hue values of 0 to 10 and between 140 to 220 (measured on a scale of 0 to 255), an increased sampling rate of 1 sample per 5 units of hue may be applied between hue values of 135 to 105 and the sampling rate can be further increased by providing multiple colour samples 101 at increments of 5 units of hue between 15 and 100. The multiple colour samples 101 taken at each selected hue consists preferably of two or three colour samples 101, however more than three colour samples 101 may be provided with the same hue value.

Unless the colour reproduction capability of the display 12 is very poor colour samples 101 within the first hue band located between 60 to 105 generally have a dominant wavelength that is perceived as green by an observer having normal colour vision and whose eyes are adapted to daylight illumination. The colour samples 101 within the second hue band located between 0 to 35 generally have a dominant wavelength that is perceived as red or orange, the colour samples 101 within the third hue band located between 105 to 135 generally have a dominant wavelength that is perceived as turquoise; the colour samples 101 within the fourth hue band located between 190 to 220 have a dominant wavelength that is perceived as purple by an observer having normal colour vision and whose eyes are adapted to daylight illumination.

Even hues defined by a dominant wavelength that falls within one of the hue bands of interest may be perceived as having a different colour than what is normally associated with the given dominant wavelength if the observer's eyes are adapted to an ambient lighting that is significantly different from daylight illumination (e.g. a fluorescent lamp is used to illuminate the room where the test takes place).

An error resulting from the poor colour reproduction capability of the display 12 or from non-ideal ambient lighting conditions can be eliminated by calibrating the colour identification test with a user having normal colour vision as explained in connection with FIG. 3.

According to a particularly preferred embodiment the calibration test is the same as the colour identification test. In this case, the calibration test may be performed before or after the test subject has performed the colour identification test. When the colour identification test is used for the purpose of calibration step S101 of FIG. 3 corresponds to step 900 of displaying instructions to ensure adaptation of the user's eyes to the ambient lighting conditions. Step S102 of displaying the colour determination exercise during the calibration test corresponds to the steps 902, 903, 904 of displaying the colour samples 101, the colour identifiers 102 and user instructions 103. Step S11 of reading user input corresponds to step 905 of reading in colour identifier 102 selections relating to the colour samples 101. Step S12 of evaluating the user input corresponds to step 906.

In step S13 of the calibration the display error resulting from the combination of the colour reproduction capability of the display 12 and the effect of the ambient lighting conditions on colour vision is determined as the difference between the expected identifier 102 based on the expected dominant wavelength of a hue and the identifier 102 actually selected by the user having normal colour vision. Based on the identifiers 102 selected by the user a modification of the colour vision test is determined in step S14 such that the diagnostically important selections of the user (test subject) possibly having colour vision deficiency will be identified base on the user's response who has normal colour vision, irrespective of the values of the hues. Accordingly, in step 906 the colour vision test is evaluated by identifying a diagnostically important selection if:

an identifier corresponding to the colour "orange" or the colour "red" is selected during the colour vision test for a displayed colour sample for which an identifier corresponding to the colour "green" is selected during the calibration test, or an identifier corresponding to the colour "green" is selected during the colour vision test for a colour sample for which an identifier corresponding to the colour "orange" or the colour "red" is selected during the calibration test, or an identifier corresponding to the colour "white" or the colour "purple" is selected during the colour vision test for a colour sample for which an identifier corresponding to the colour "turquoise" is selected during the calibration test, or an identifier corresponding to the colour "turquoise" is selected during the colour vision test for a colour sample for which an identifier corresponding to the colour "purple" is selected during the calibration test.

Furthermore, a diagnostically important selection may be identified if:

an identifier corresponding to the colour "orange" or the colour "red" is selected during the colour vision test for a displayed colour sample for which an identifier corresponding to the colours "turquoise", "blue" or "purple" is selected during the calibration test, or an identifier corresponding to the colour "white" is selected during the colour vision test for a colour sample for which an identifier corresponding to the colour "blue" is selected during the calibration test.

Preferably, the expected colour of the colour samples 101 are taken into account during the calibration test such that a critical number of permitted deviations from the expected colours is defined (preferably at least 5% of the number of colour samples 101, more preferably at least 10%, even more preferably 10 to 20%), none of which may correspond to a diagnostically important selection without calibration. In the context of the present invention the expected colour of a colour sample is defined as the colour of the dominant wavelength of the hue of the colour sample calculated with colour gamut triangle 92 of the colour space of an sRGB display 12 using the CIE Standard illuminant D65 as the white point C. If the selections made by the user performing the calibration test exceeds the critical number of permitted deviations or the user makes a diagnostically important selection then this indicates that either the user does not have normal colour vision, or the colour reproduction capability of the display 12 is too poor, or the ambient lighting conditions are unsuitable for colour vision measurement. In either case the results of the calibration test are preferably discarded and the possible sources of errors are displayed to the user.

The colour identification test is implemented in the form of one or more computer programs. The computer program is a software containing computer instructions which when executed by the processor 16 of the computer 10 cause the computer 10 to carry out some or all steps of the colour identification test. Since the term "computer" is defined in a broad sense, the term "computer program" also includes various software, e.g. desktop computer programs, tablet and smart phone applications, etc.

The computer program may be a dedicated software or it may be a web application (e.g. a JAVA script application) run by a web browser of the computer 10. According to a preferred embodiment only the steps preceding the evaluation of the test are carried out by the computer program running on the computer 10 of the user, the step of evaluating the test is carried out by a separate computer running on a remote computer 10 (e.g. a remote server or a cloud server).

The invention further relates to the computer 10 which stores such a computer program in its non-volatile storage medium 17.

The above described colour identification test is preferably used to supplement the colour discrimination test described above or any other colour discrimination test which uses at least one target mark having a target hue, a set of first test marks each having a hue corresponding to the target hue and a set of second test marks each having a test hue that is located in a chromaticity diagram on a common confusion line of a type of cone receptor with the target hue. For example, the Ishihara test is such a colour discrimination test as well as the above described colour discrimination test according to the present invention. It should be appreciated that any number of further test marks may be applied which have hues differing both from the target hue and the test hue. The brightness of the at least one target mark and test marks may also vary e.g. as explained above in connection with the colour discrimination test of the present invention.

The colour discrimination test is used to determine whether or not the test subject has a colour vision deficiency of a type of cone receptor (typically L-cone or M-cone) to which the colour discrimination test relates and the colour identification test is used to determine whether or not the colour vision deficiency is severe, i.e. anopia or a condition close to anopia. The inventors of the present invention have found that the colour discrimination tests are generally suitable to reliably determine if the test subject has a colour vision deficiency, however, the tests based on hue pairs on a common confusion line (pseudo-isochromatic hue pairs) are less reliable or incapable of differentiating severe cases from moderate and mild cases. The reason for this is that the colour discrimination tests contain tasks where the test subject has to discriminate between two hues that are located on a common confusion line of a chromaticity diagram, typically on a common confusion line that traverses a white point of the chromaticity diagram. Severe cases of colour vision deficiency would be indicated by the fact that hues lying very far apart from each other along the common confusion line are confused as well. In particular, if a confusion line is used that traverses the white point then the two hues must lie on opposite sides of the white point and severe colour vision deficiency is indicated by confusing hues that lie far from the white point as well as from each other. However, due to errors associated with displaying the theoretically determined hue pairs the actual hues displayed are only close to the selected confusion line but do not lie exactly thereon. The further the hues are from white point the larger the deviation from the selected confusion line which may have for effect that the actually displayed hues are no longer pseudo-isochromatic, whereby a user with severe colour vision deficiency (even an anope) may be able to distinguish between the actually displayed hues, although the theoretical hues lying on the common confusion line would not be distinguishable by the same user. This problem can be overcome by the colour identification test of the present invention, which is designed to detect symptoms of sever colour vision deficiency.

According to a preferred embodiment the colour vision test including a colour discrimination test and the colour identification test is supplemented by a calibration test corresponding to the colour identification test. The calibration test is performed as described above and used to modify the evaluation of the colour identification test as described above.

According to a further preferred embodiment the colour vision test is supplemented by a calibration test corresponding to the colour discrimination test, such that the number of incorrect selections made by a user having normal colour vision in connection with each type of cone receptor being tested is subtracted from the number of incorrect selections made in connection with the same type of cone receptor by a test subject potentially having colour vision deficiency. For example, if L-cones are being tested by the calibration test and the colour discrimination test then subtracting the number of incorrect responses of the user with normal colour vision made in connection with colour discrimination tasks testing colour vision deficiency of the L-cones from the number of incorrect responses of the test subject performing the colour vision test made in connection with the same colour discrimination tasks. If M-cones are also being tested by the calibration test and the colour discrimination test then subtracting the number of incorrect responses of the user with normal colour vision made in connection with colour discrimination tasks testing colour vision deficiency of the M-cones from the number of incorrect responses of the test subject made in connection with the same colour discrimination tasks. In practice the colour vision deficiency of the L-cones are tested with hue pairs selected from a common protanope confusion line and the M-cones are tested with hue pairs selected from a common deuteranope confusion line. Similarly, the S-cones may be tested with hue pairs selected from a common tritanope confusion line, however, such colour discrimination tasks are preferably used for calibration purposes as tritanomaly is extremely rare.

According to another preferred embodiment both the colour identification test and the colour discrimination test are calibrated with calibration tests corresponding to the colour identification test and the colour discrimination test as explained above.

The colour vision test comprising the combination of the colour discrimination test and the colour identification test is also implemented in the form of one or more computer programs. The computer program may be a dedicated software or it may be a web application (e.g. a JAVA script application) run by a web browser of the computer 10. According to a preferred embodiment only the steps preceding the evaluation of the test are carried out by the computer program running on the computer 10 of the user, the step of evaluating the test is carried out by a separate computer running on a remote computer 10 (e.g. a remote server or a cloud server).The invention further relates to the computer 10 which stores such a computer program in its non-volatile storage medium 17.

Various modifications to the above disclosed embodiments will be apparent to a person skilled in the art without departing from the scope of protection determined by the attached claims.

The invention claimed is:

1. A computer implemented method of testing colour vision by displaying a colour vision test on a display of a computer having at least one input interface, the method comprising:
   selecting a target colour having a target hue and a target brightness and a test colour having a test hue such that the target colour and the test colour correspond in a chromaticity diagram of a colour space to two colours of different hue located on a common confusion line of a selected type of dichromacy;
   providing a target image consisting of a set of target marks having a hue corresponding to the target hue and having an average brightness corresponding to the target brightness;
   providing a plurality of test images comprising:
      a first test image comprising a set of first test marks having a hue corresponding to the target hue and having an average brightness that is different from the target brightness,
      a second test image comprising a set of second test marks having a hue corresponding to the test hue and having an average brightness corresponding to the target brightness,
      any number of third test images each comprising a set of third test marks having a hue corresponding to the test hue and having an average brightness that is different from the target brightness,
   displaying the target image in a target region of the display and displaying the plurality of test images at a plurality of test regions of the display that are spaced from the target region and from each other,
   displaying instructions to select one of the plurality of test images based on highest similarity of hue compared to the target image,
   reading in user input through the at least one input interface of the computer relating to the selection of a selected test image, and
   evaluating the colour vision test such that if the selected test image corresponds to the first test image then determining a correct selection, and if the selected test image corresponds to one of the second test image or the third test images then determining an incorrect selection.

2. The computer implemented method according to claim 1, comprising selecting the target colour and test colour such that the common confusion line traverses a white point of the chromaticity diagram and the target colour and the test colour are located on opposite sides of the common confusion line with respect to the white point.

3. The computer implemented method according to claim 2, comprising selecting a plurality of pairs of target colour and test colour located on the common confusion line of the selected type of dichromacy such that a distance of the target colour and the test colour measured along the common confusion line of the selected type of dichromacy differs for at least two, preferably for at least five colour pairs, repeating the colour vision test with the plurality of pairs of target colour and test colour, and evaluating a plurality of colour vision tests by determining a number of incorrect user selections.

4. The computer implemented method according to claim 3, comprising determining a colour vision deficiency caused by a disorder of a type of cone receptors responsible for the selected type of dichromacy if the number of the incorrect user selections exceeds a threshold.

5. The computer implemented method according to claim 3, comprising selecting a first group of the plurality of pairs of target colour and test colour for which the selected type of dichromacy is protanopia and the common confusion line is a protanope confusion line and selecting a second group of the plurality of pairs of target colour and test colour for which the selected type of dichromacy is deuteranopia and the common confusion line is a deuteranope confusion line, repeating the colour vision test with the first group of the plurality of pairs of target colour and test colour and with the second group of the plurality of pairs of target colour and test colour, and evaluating the plurality of colour vision tests by determining a number of incorrect user selections within the first group of the plurality of pairs of target colour and test colour and a number of incorrect user selections within the second group of the plurality of pairs of target colour and test colour.

6. The computer implemented method according to claim 5, comprising determining a colour vision deficiency relating to a disorder of L-cones if the number of the incorrect user selections within the first group exceeds the number of the incorrect user selections within the second group by a first threshold; and determining a colour vision deficiency relating to a disorder of M-cones if the number of the incorrect user selections within the second group exceeds the number of the incorrect user selections within the first group by a second threshold.

7. A computer implemented method of testing colour vision by displaying a colour vision test on a display of a computer having at least one input interface, the method comprising:
   providing a plurality of colour samples, each colour sample having a hue between 0 to 220 on a scale of 0 to 255;
   displaying the plurality of colour samples on the display;
   displaying on the display a set of identifiers each corresponding to a different colour;
   displaying on the display instructions to select for each colour sample an identifier from the set of displayed identifiers corresponding to the hue of the colour sample, and
   reading in for each colour sample user input through the at least one input interface of the computer relating to a selection of the identifier corresponding to the hue of the colour sample.

8. The computer implemented method according to claim 7, comprising evaluating the colour vision test by identifying a diagnostically important selection if:
   an identifier corresponding to a colour "orange" or a colour "red" is selected for a displayed colour sample having a hue value between 60 to 220, or
   an identifier corresponding to a colour "green" is selected for a colour sample having a hue value between 0 to 35, or
   an identifier corresponding to a colour "white" is selected for a colour sample having a hue value between 105 to 150, or
   an identifier corresponding to a colour "purple" is selected for a colour sample having a hue value between 105 to 135, or
   an identifier corresponding to a colour "turquoise" is selected for a colour sample having a hue value between 190 to 220.

9. A method of calibrating a colour vision test for testing colour vision under ambient lighting conditions, wherein the colour vision test is to be displayed on a colour display of a computer having at least one input interface, characterised by
　displaying a calibration test on the display under the ambient lighting conditions for a user with normal colour vision,
　displaying within at least one measuring region of the display a colour determination task requiring user input as a part of the calibration test,
　reading the user input through at least one input interface of the computer,
　evaluating the user input and determining as a result of the evaluation a display error resulting from a combination of a colour reproduction capability of the display and an effect of the ambient lighting conditions on colour vision, and
　determining a modification to the colour vision test from the display error that corrects the colour vision test with respect to the display error.

10. The method according to claim 9, characterised by displaying a colour determination task that requires a user input relating to determination by the user of an intensity of at least a first coloured subpixels selected from red, green and blue subpixels of pixels of the at least one measuring region via the at least one user input interface of the computer,
　reading the user input relating to the determination of the intensity of at least the first coloured subpixels via the at least one input interface,
　evaluating the user input relating to the determination of the intensity of at least the first coloured subpixels, and as a result of the evaluation determining the display error in respect of at least the first coloured subpixels, wherein the display error is a deviation from a reference colour corresponding to a first colour resulting from the combination of the colour reproduction capability of the display and of the effect of the ambient lighting conditions exerted on vision of the first colour.

11. The method according to claim 10, characterised by displaying a colour determination task during which a colour has to be set or selected within the at least one measuring region of the display by the user by setting or selecting the intensity of at least the first coloured subpixels using the at least one input interface, and reading as user input data relating to the intensity setting or selection of at least the first coloured subpixels via the at least one input interface.

12. The method according to claim 10, characterised by displaying a colour determination task during which white or yellow colour has to be set within the at least one measuring region of the display by the user by setting intensity of at least, the red subpixels and the green subpixels using the at least one input interface, and during the evaluation determining the display error determining a difference in intensity of the red subpixels and the green subpixels within the at least one measuring region of the display from read setting data, and regarding the difference as the display error.

13. The method according to claim 10, characterised by displaying a colour determination task during which purple or turquoise colours have to be set within the at least one measuring region of the display by the user by setting intensity of the red subpixels and the blue subpixels or the green subpixels and the blue subpixels using the at least one input interface, and during the evaluation determining the display error determining a difference in intensity of the red subpixels and the blue subpixels or the green subpixels and the blue subpixels within the at least one measuring region of the display from read setting data, and regarding the difference as the display error.

14. The method according to claim 9, characterised by providing instructions for the user with normal colour vision during the calibration test before performing the colour determination task to look at an object known to be white for a few minutes, preferably a white sheet of paper, preferably for at least 2 minutes, optimally for 10 minutes.

15. The method according to claim 14, characterised by, displaying a colour determination task during which white colour corresponding to a colour of the object has to be set within the at least one measuring region of the display by the user by setting intensity of at least red subpixels and green subpixels selected from the red subpixels, the green subpixels and blue subpixels of pixels of the at least one measuring region using the at least one input interface, reading setting data relating to the intensity of the red subpixels and the green subpixels through the at least one input interface as the user input, and during the evaluation determining a difference of the intensity of the green subpixels and the red subpixels within the at least one measuring region of the display from the read setting data, and regarding the difference as the display error.

16. The method according to claim 9, characterised by checking whether the display has subpixels of fourth colour apart from red, green and blue subpixels, and if so setting intensity of the subpixels of fourth colour to zero at least within the at least one measuring region during the displaying of the colour determination task.

17. The method according to claim 9, characterized by
　performing the determined modification to the colour vision test,
　displaying the colour vision test on the display,
　displaying a second colour determination task requiring second user input within the at least a one measuring region of the display as a part of the colour vision test,
　reading the second user input through the at least one input interface of the computer,
　evaluating the second user input, and determining as a result of the evaluation of the second user input a colour vision of the user performing the colour vision test.

18. The method according to claim 17, characterised by determining a modification to display parameters of the colour vision test as the modification to the colour vision test which corrects the colour vision test with respect to the display error when the colour vision test is displayed on the display, and accordingly modifying the display parameters of the colour vision test when the colour vision test is modified, or determining a modification to evaluation parameters of the colour vision test as the modification to the colour vision test which corrects a measurement result obtained with the colour vision test with respect to the display error when evaluating the colour vision test, and when modifying the colour vision test the evaluation parameters of the colour vision test are modified accordingly.

19. The method according to claim 17, characterised by the calibration test being same as the colour vision test.

20. A computer comprising a colour display, at least one input interface, at least one processor and a non-volatile storage medium storing a computer program containing computer instructions, the computer program being configured such as to cause the computer to carry out the method according to claim 9 when said computer instructions are executed by the at least one processor.

* * * * *